US011478493B2

(12) United States Patent
Xu et al.

(10) Patent No.: US 11,478,493 B2
(45) Date of Patent: Oct. 25, 2022

(54) FABRICATION AND APPLICATION OF A HETERO-TARGETED NANO-COCKTAIL WITH TRACELESS LINKERS

(71) Applicant: UNIVERSITY OF SOUTH CAROLINA, Columbia, SC (US)

(72) Inventors: Peisheng Xu, Chapin, SC (US); Binglin Sui, Columbia, SC (US)

(73) Assignee: University of South Carolina, Columbia, SC (US)

( * ) Notice: Subject to any disclaimer, the term of this patent is extended or adjusted under 35 U.S.C. 154(b) by 181 days.

(21) Appl. No.: 16/735,977

(22) Filed: Jan. 7, 2020

(65) Prior Publication Data

US 2020/0281955 A1  Sep. 10, 2020

Related U.S. Application Data

(60) Provisional application No. 62/815,423, filed on Mar. 8, 2019.

(51) Int. Cl.
| | |
|---|---|
| *A61K 31/704* | (2006.01) |
| *A61K 47/34* | (2017.01) |
| *A61K 9/06* | (2006.01) |
| *A61K 45/06* | (2006.01) |
| *A61P 35/00* | (2006.01) |
| *A61K 47/68* | (2017.01) |
| *A61K 47/54* | (2017.01) |
| *A61K 9/14* | (2006.01) |
| *A61K 31/337* | (2006.01) |

(52) U.S. Cl.
CPC .............. *A61K 31/704* (2013.01); *A61K 9/06* (2013.01); *A61K 9/14* (2013.01); *A61K 31/337* (2013.01); *A61K 45/06* (2013.01); *A61K 47/34* (2013.01); *A61K 47/542* (2017.08); *A61K 47/6849* (2017.08); *A61P 35/00* (2018.01)

(58) Field of Classification Search
CPC .. A61K 31/704; A61K 31/337; A61K 47/542; A61K 47/6849; A61K 47/34; A61K 9/06; A61K 9/14; A61K 45/06; A61P 35/00
See application file for complete search history.

(56) References Cited

U.S. PATENT DOCUMENTS

| | | | |
|---|---|---|---|
| 2012/0213698 A1* | 8/2012 | Petersen ............. | A61K 51/1234 424/1.37 |
| 2014/0011760 A1* | 1/2014 | Xu ......................... | C08F 216/04 514/34 |
| 2015/0328254 A1* | 11/2015 | Heller ................... | A61K 31/517 424/9.1 |
| 2018/0355044 A1* | 12/2018 | Jiang ...................... | A61K 35/17 |

OTHER PUBLICATIONS

Banergee et al., Int J Cancer, Nov. 2, 2004, 112(4): 693-700. (Year: 2004).*

Guo et al. J. Nanobiotech., 16, 74, 2018. (Year: 2018).*
Ahmed, et al. "Biodegradable polymersomes loaded with both paclitaxel and doxorubicin permeate and shrink tumors, inducing apoptosis in proportion to accumulated drug" *J. Contr. Rel.* 116 (2006) pp. 150-158.
Al-Eisawi, et al. "Carboplatin and oxaliplatin in sequenced combination with bortezomib in ovarian tumour models" *J. Ovar. Res.* 6 (2013) pp. 1-11.
Bahadur, et al. "Redox Potential Ultrasensitive Nanoparticle for the Targeted Delivery of Camptothecin to HER2-Positive Cancer Cells" *Mol. Pharm.* 11 (2014) pp. 1897-1905.
Bahadur, et al. "Multicompartment Intracellular Self-Expanding Nanogel for Targeted Delivery of Drug Cocktail" *Adv. Mater.* 24 (2012) pp. 6479-6483.
Bayo, et al. "Toxicity of docetaxel, carboplatin, and trastuzumab combination as adjuvant or neo-adjuvant treatment for Her2 positive breast cancer patients and impact of colony-stimulating factor prophylaxis" *Breast J.* 24 (2018) pp. 462-467.
Caraglia, et al. "Chemotherapy Regimen GOLF Induces Apoptosis in Colon Cancer Cells through Multi-Chaperone Complex Inactivation and Increased Raf-1 Ubiquitin-Dependent Degradation" *Canc. Biol. Ther.* 4 (2005) pp. 1159-1167.
Chen, et al. "Pluronic-based functional polymeric mixed micelles for co-delivery of doxorubicin and paclitaxel to multidrug resistant tumor" *Int. J. Pharm.* 488 (2015) pp. 44-58.
Chen, et al. "Dual-Targeting Pro-apoptotic Peptide for Programmed Cancer Cell Death via Specific Mitochondria Damage" *Sci. Rep.* 3:3468 (2013) pp. 1-7.
Cheng, et al. "Repurposing suramin for the treatment of breast cancer lung metastasis with glycol chitosan-based nanoparticles" *Acta Biomater.* 84 (2018) pp. 378-390.
Cho, et al. "Intraperitoneal delivery of platinum with in-situ crosslinkable hyaluronic acid gel for local therapy of ovarian cancer" *Biomater.* 37 (2015) pp. 312-319.
Cho, et al. "Injectable poly(organophosphazene)-camptothecin conjugate hydrogels: synthesis, characterization, and antitumor activities" *Eur. J. Pharm. Biopharm.* 81 (2012) pp. 582-590.
Da Silva, et al. "Comparative Effectiveness and Safety of Monoclonal Antibodies (Bevacizumab, Cetuximab, and Panitumumab) in Combination with Chemotherapy for Metastatic Colorectal Cancer: A Systematic Review and Meta-Analysis" *BioDrugs* 32 (2018) pp. 585-606.
Duan, et al "Smart pH-sensitive and temporal-controlled polymeric micelles for effective combination therapy of doxorubicin and disulfiram" *ACS Nano* 7 (2013) pp. 5858-5869.
Fang, et al. "The EPR effect: Unique features of tumor blood vessels for drug delivery, factors involved, and limitations and augmentation of the effect" *Adv. Drug Deliv. Rev.* 63 (2011) pp. 136-151.
Grunberg, et al. "Effectiveness of a single-day three-drug regimen of dexamethasone, palonosetron, and aprepitant for the prevention of acute and delayed nausea and vomiting caused by moderately emetogenic chemotherapy" *Supp. Care Canc.* 17 (2009) pp. 589-594.

(Continued)

*Primary Examiner* — Genevieve S Alley
(74) *Attorney, Agent, or Firm* — Dority & Manning, P.A.

(57) ABSTRACT

A hetero-targeted, dual-responsive nanogel to deliver chemotherapeutic agents to a metastatic cancer is provided. The nanogel includes a first chemotherapeutic agent, a second chemotherapeutic agent, a first targeting ligand, and a second targeting ligand. A method of treating cancer in a mammal with the nanogel are also provided.

17 Claims, 14 Drawing Sheets

(56) References Cited

OTHER PUBLICATIONS

He, et al. "Repurposing Disulfiram for Cancer Therapy via Targeted Nanotechnology through Enhanced Tumor Mass Penetration and Disassembly" Acta Biomater. 68 (2018) pp. 113-124.

He, et al. "Triple-responsive expansile nanogel for tumor and mitochondria targeted photosensitizer delivery" Biomater. 35 (2014) pp. 9546-9553.

Huang, et al. "Sigma-2 Receptor Ligands and Their Perspectives in Cancer Diagnosis and Therapy" Med. Res. Rev. 34 (2014) pp. 532-566.

Kibria, et al. "Dual-ligand modification of PEGylated liposomes shows better cell selectivity and efficient gene delivery" J. Contr. Rel. 153 (2011) pp. 141-148.

Maeda, et al. "EPR Effect Based Drug Design and Clinical Outlook for Enhanced Cancer Chemotherapy" Adv. Drug Deliv. Rev. 63 (2011) pp. 129-192.

Masui, et al. "A tale of two approaches: complementary mechanisms of cytotoxic and targeted therapy resistance may inform next-generation cancer treatments" Carcinogenesis 34 (2013) pp. 725-738.

Meng, et al. "Reduction-sensitive polymers and bioconjugates for biomedical applications" Biomater. 30 (2009) pp. 2180-2198.

Peluso, J.J. "Progesterone signaling mediated through progesterone receptor membrane component-1 in ovarian cells with special emphasis on ovarian cancer" Steroids 76 (2011) pp. 903-909.

Pinhassi, et al. "Arabinogalactan-Folic Acid-Drug Conjugate for Targeted Delivery and Target-Activated Release of Anticancer Drugs to Folate Receptor-Overexpressing Cells" Biomacromol. 11 (2010) pp. 294-303.

Qi, et al. "Efficacy and toxicity of molecular targeted therapies in combination with docetaxel for metastatic castration-resistant prostate cancer: a meta-analysis of phase III randomized controlled trials" J. Chemother. 27 (2015) pp. 181-187, (Abstract only).

Sato, et al. "Combination chemotherapy of oxaliplatin and 5-fluorouracil may be an effective regimen for mucinous adenocarcinoma of the ovary: A potential treatment strategy" Canc. Sci. 100 (2009) pp. 546-551.

Saul, et al. "A dual-ligand approach for enhancing targeting selectivity of therapeutic nanocarriers" J. Contr. Rel. 114 (2006) pp. 277-287.

Slamon, et al. "Studies of the HER-2/neu proto-oncogene in human breast and ovarian cancer" Science 244 (1989) pp. 707-712.

Tang, et al. "Synergistic targeted delivery of pay load into tumor cells by dual-ligand liposomes co-modified with cholesterol anchored transferrin and TAT" Int'l. J. Pharm. 454 (2013) pp. 31-40.

Tas, et al. "Same Chemotherapy Regimen Leads to Different Myelotoxicity in Different Malignancies: A Comparison of Chemotherapy-Associated Myelotoxicity in Patients with Advanced Ovarian and Non-Small-Cell Lung Cancer" Am. J. Therapeutics 23 (2016) pp. e670-e679.

Wang, et al. "Enhanced anti-tumor efficacy by co-delivery of doxorubicin and paclitaxel with amphiphilic methoxy PEG-PLGA copolymer nanoparticles" Biomater. 32 (2011) pp. 8281-8290.

Xiao, et al. "The effect of surface charge on in vivo biodistribution of PEG-oligocholic acid based micellar nanoparticles" Biomater. 32 (2011) pp. 3435-3446.

Yu, et al. "Targeted drug delivery and cross-linking induced apoptosis with anti-CD37 based dual-ligand immunoliposomes in B chronic lymphocytic leukemia cells" Biomater. 34 (2013) pp. 6185-6193.

Zeng, et al. "Sigma-2 receptor ligand as a novel method for delivering a SMAC mimetic drug for treating ovarian cancer" Br. J. Canc. 109 (2013) pp. 2368-2377.

Zhou, et al. "Charge-Reversal Drug Conjugate for Targeted Cancer Cell Nuclear Drug Delivery" Adv. Funct. Mater. 19 (2009) pp. 3580-3589.

Zou, et al. "Poly(ethylene oxide)-block-polyphosphoester-graft-paclitaxel conjugates with acid-labile linkages as a pH-sensitive and functional nanoscopic platform for paclitaxel delivery" Adv. Healthc. Mater. 3 (2014) pp. 441-448.

* cited by examiner

FABRICATION AND APPLICATION OF A HETERO-TARGETED NANO-COCKTAIL WITH TRACELESS LINKERS

PRIORITY INFORMATION

The present application claims priority to U.S. Provisional Patent Application Ser. No. 62/815,423, filed on Mar. 8, 2019, the disclosure of which is incorporated by reference herein.

STATEMENT AS TO RIGHTS TO INVENTIONS MADE UNDER FEDERALLY SPONSORED RESEARCH

This invention was made with Government support under grant number R15CA188847, awarded by the National Institutes of Health, and grant number R01AG054839, also awarded by the National Institutes of Health. The Government has certain rights in the invention.

BACKGROUND TO THE INVENTION

Ovarian cancer is the most lethal form of cancer among women, accounting for 3% of all cancer cases at 20,000 per year. Metastatic ovarian cancer is an advanced stage malignancy often spreading to the liver, the lungs, the spleen, the intestines, the brain, or the lymph nodes around the body. Metastasis involves multiple steps, including cell invasion from the primary tumor, intravasation and extravasation in the circulation system, and growth in the distant location. In such cases, early detection is preferable but is often hampered by a lack of appropriate tumor markers and clinically relevant symptoms typically associated with cancer at the primary site. Early-stage detection garners a 5-year survival rate of 92%; however, due to a lack of symptoms, late diagnoses are often a hallmark of this disease, leading to a 30% survival rate. Currently, various treatments are available for a patient to use, varying based on the state of metastasis. Although the various treatments exist, including chemotherapy, hormone therapy, surgery, and radiation therapy, there is still a lack of a targeted, minimally invasive treatment option.

Due to the heterogeneous nature of tumors and the limitation of anticancer drugs, a mono-compound treatment can usually only kill a fraction of cancer cells, sparing non-responsive cells which can continue proliferating and result in cancer recurrence. To address the inadequacy of a single drug, a drug combination (i.e., "drug cocktail") can be utilized that includes multiple anticancer drugs of different anticancer mechanisms. Despite many promising in vitro and in vivo results achieved with a drug cocktail in cancer animal models, translation of the drug cocktail concept into a successful cancer treatment remains a challenge due to the lack of a safe and effective delivery system.

Previous research has been directed to a two-drug cocktail nanogel system by encapsulating drugs through hydrophobic interaction with a pH and redox potential dual responsive poly[(2-(pyridin-2-yldisulfanyl) ethyl acrylate)-co-[poly (ethylene glycol)]] (PDSA-PEG) polymer. It was found that the premature release of the encapsulated drugs during circulation can be reduced while significantly boosting the drugs' discharge in acidic pH or other reducing environments. Furthermore, the nano-cocktail exhibits a synergistic effect for killing cancer cells. However, the nanogel-based system could attenuate drug burst release, resulting in about 20% of the drugs being released before reaching the target tissue, which could potentially deteriorate the health condition of an already compromised cancer patient. Additionally, the ratio between the two compounds in the nano-cocktail could not be freely tuned according to their required potencies due to the constraint of their relative hydrophobicities.

To further minimize premature release-induced side effects, polymer drug conjugate-based nanoparticles, in which drug molecules are linked with a polymer carrier via covalent bonds, including hydrazone bonds, ester bonds, amide bonds, and disulfide bonds, have attracted a lot of attention. Since the loaded drug can only be released when the linker is cleaved, the systemic toxicity of the drug can be greatly reduced. Before conjugation onto a polymer, most drugs must be modified first to introduce a functional group. Consequently, after the break of the linker, the liberated molecules from the polymer are not in their original therapeutic form, which results in significantly diminished potency. Thus, the theoretic advantages of drug cocktails are locked in a catch-22 dilemma between safety and efficacy.

As such, there exists a need for a drug delivery system that can target specific cancer cells, deliver the drug safely, and provide the most effective form of treatment without initiating a toxicity response.

SUMMARY OF THE INVENTION

According to one particular embodiment of the present invention, a nanogel for use as a drug cocktail is provided. The nanogel includes a first chemotherapeutic agent, a second chemotherapeutic agent, a first targeting ligand, and a second targeting ligand.

In one embodiment, the nanogel can include a polymeric carrier, which can include a copolymer of an ethyl acrylate and an ethylene oxide. Further, the ethyl acrylate can include poly[(2-(pyridin-2-yldisulfanyl) ethyl acrylate), (pyridine-2-thiol)ethyl acrylate, (pyridine-2-thiol) ethyl methacrylate, ethyl (2-(pyridin-2-yldisulfanyl)ethyl) carbonate, N-(2-(pyridin-2-yldisulfanyl)ethyl) acrylamide, or a combination thereof. Meanwhile, the ethylene oxide can include polyethylene glycol.

In another embodiment, the first chemotherapeutic agent can be different from the second chemotherapeutic agent. Further, the first chemotherapeutic agent and the second chemotherapeutic agent can be selected from the group consisting of doxorubicin, paclitaxel, daunorubicin, valrubicin, triptolide, epirubicin, idarubicin, docetaxel, cisplatin, carboplatin, oxaliplatin, camptothecin, vincristine, vinblastine, 5-fluorouracil (5-FU), mitomycin, cyclophosphamide, methotrexate, mitoxantrone, topotecan, capecitabine, doxifluridine, irinotecan, tegafur, chlorambucil, belotecan, anastrozole, tamoxifen, GLEEVEC® (imatinib), floxuridine, leuprolide, flutamide, zoledronate, streptozocin, vinorelbine, hydroxyurea, retinoic acid, mechlorethamine, busulfan, prednisone, testosterone, aspirin, salicylates, ibuprofen, naproxen, fenoprofen, indomethacin, phenyltazone, mechlorethamine, dexamethasone, prednisolone, celecoxib, valdecoxib, nimesulide, cortisone, corticosteroid, gemcitabine, cedrol, or a combination thereof.

In yet another embodiment, the first chemotherapeutic agent can include a taxane. Further, the taxane can be paclitaxel.

In still another embodiment, the second chemotherapeutic agent can include an anthracycline. Further, the anthracycline can be doxorubicin.

In one more embodiment, the first targeting ligand can be different from the second targeting ligand. Further, the first targeting ligand and the second targeting ligand can be selected from the group consisting of 4-methoxybenzamide, Anti-ErbB2 AFFIBODY® molecule, anti-EGFR AFFIBODY® molecule, folic acid, 0-d-glucose, Asn-Gly-Arg peptide, Angiopep2, HERCEPTIN®, transferrin, arginine-glycine-aspartate peptide, lactobionic acid, or a combination thereof.

In an additional embodiment, the first targeting ligand can include 4-methoxybenazmine and the second targeting ligand can include Anti-ErbB2 AFFIBODY® molecule.

In another embodiment, the molar ratio of the first chemotherapeutic agent to the second chemotherapeutic agent can range from about 1:1 to about 1:1000.

In one more embodiment, the average particle size of the nanogel can range from about 50 nanometers to about 150 nanometers.

In still another embodiment, the nanogel can have a surface charge ranging from about −1 millivolts to about −50 millivolts.

In one more embodiment of the present invention, a method of treating a cancerous area in a mammal utilizing targeting ligands to target only cancerous cells within the cancerous area is provided. The method includes delivering a nanogel having traceless linkers to the cancerous area, wherein more than one chemotherapeutic agent is then released from the nanogel, the nanogel comprising a polymeric carrier; a first chemotherapeutic agent; a second chemotherapeutic agent that is different from the first chemotherapeutic agent, a first targeting ligand, and a second targeting ligand that is different from the first targeting ligand.

In one embodiment, the first targeting ligand can be a benzamide comprising 4-methoxybenzamide.

In still another embodiment, the second targeting ligand can be an AFFIBODY® molecule that includes Anti-ErbB2 AFFIBODY® molecule.

In yet another embodiment, the first chemotherapeutic agent and the second chemotherapeutic agent can be selected from the group consisting of doxorubicin, paclitaxel, daunorubicin, valrubicin, triptolide, epirubicin, idarubicin, docetaxel, cisplatin, carboplatin, oxaliplatin, camptothecin, vincristine, vinblastine, 5-fluorouracil(5-FU), mitomycin, cyclophosphamide, methotrexate, mitoxantrone, topotecan, capecitabine, doxifluridine, irinotecan, tegafur, chlorambucil, belotecan, anastrozole, tamoxifen, GLEEVEC® (imatinib), floxuridine, leuprolide, flutamide, zoledronate, streptozocin, vinorelbine, hydroxyurea, retinoic acid, mechlorethamine, busulfan, prednisone, testosterone, aspirin, salicylates, ibuprofen, naproxen, fenoprofen, indomethacin, phenyltazone, mechlorethamine, dexamethasone, prednisolone, celecoxib, valdecoxib, nimesulide, cortisone, corticosteroid, gemcitabine, cedrol, or a combination thereof.

In another embodiment, the traceless linkers can include a thiol group.

Other features and aspects of the present invention are set forth in greater detail below.

Figure 1A:
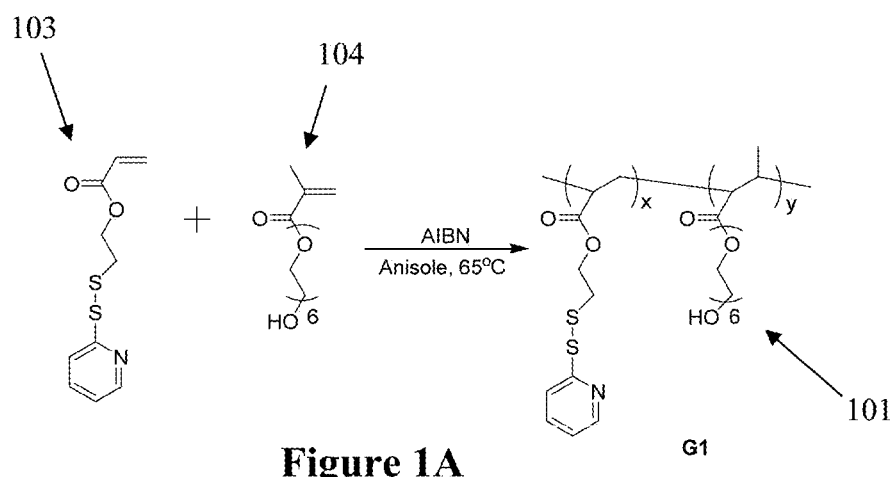
FIG. 1A illustrates the synthesis of polymer PDSA-PEG1.

Repeat use of reference characters in the present specification and drawings is intended to represent the same or analogous features or elements of the present invention.

DETAILED DESCRIPTION

Reference will now be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only and is not intended as limiting the broader aspects of the present invention, which broader aspects are embodied exemplary constructions.

Generally speaking, the present invention is directed to the synthesis of a nanogel designed to seamlessly release cancer drugs to targeted cancerous sites without encountering common problems associated with drug release strategies, such as toxicity and low potency of the delivered drug. In one such embodiment, the nanogel system is directed to the treatment of ovarian cancer in mammals in a safe and direct method. The various components of the nanogel system of the present invention, the method of forming the nanogel system, and the method of treating a mammal with the nanoparticle system are discussed in more detail below.

Figure 4A:
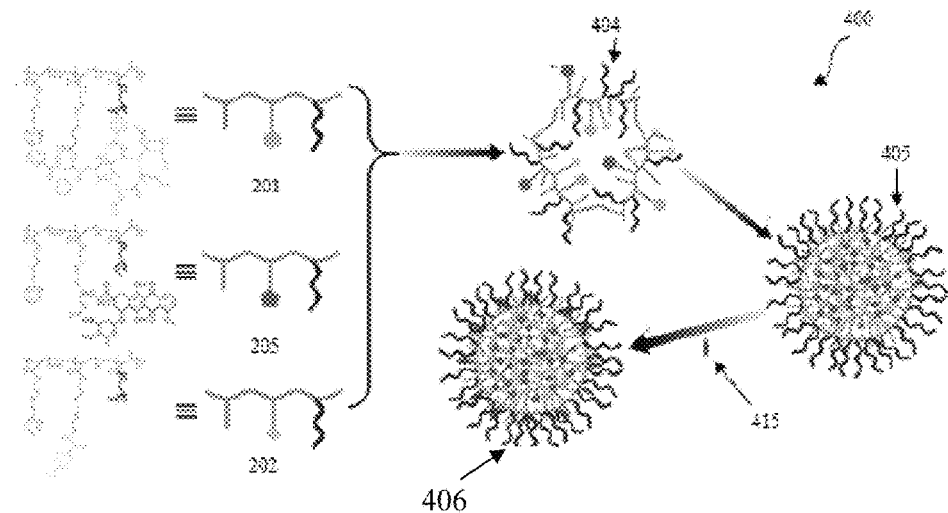
FIG. 4A illustrates a fabrication scheme of PPP, PPPM, PPD, PPPD, and PPPDM nanogels, and AEB-conjugated PPDSA, PPPDSA, and PPPDMA nanogels.
Figure 4B:
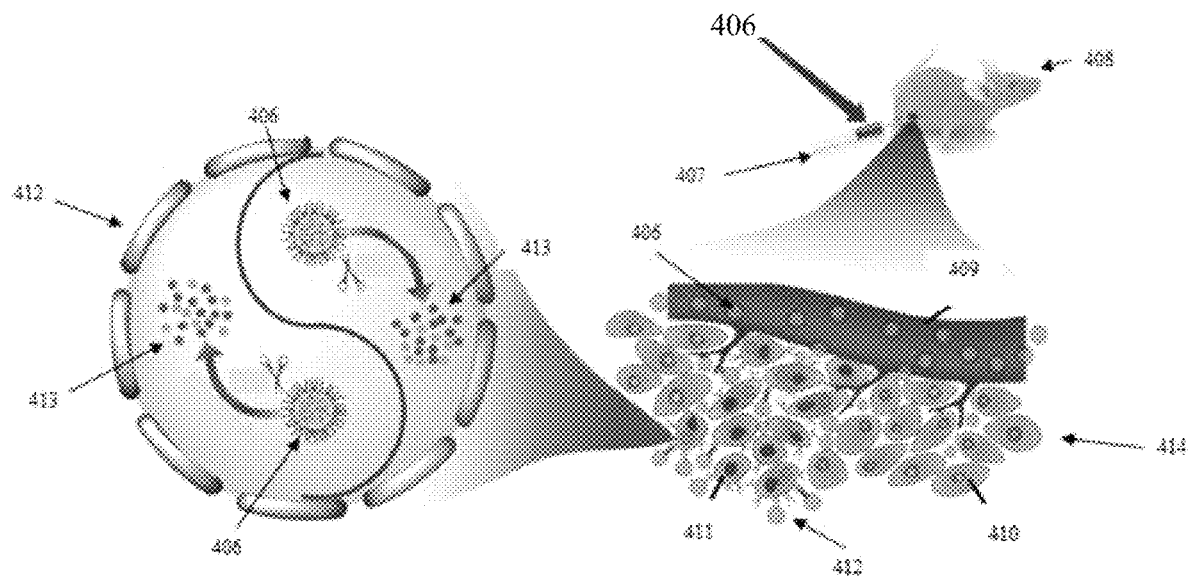
FIG. 4B is a graph illustrating the dual-stimuli-responsive drug release in cancer cells.

In one embodiment as showcased by FIG. 4A, the nanogel system 400 of the present invention can include three or more polymeric carriers 201, 202, and 205 being crosslinked through disulfide bonds 404, which are self-assembled into a spherical structure 405, and decorated with an affinity ligand 415 to form a final nanogel 406. Referring to FIG. 4B, the nanogel 406 can be injected into a mammal 408 via syringe 407 or other suitable drug delivery means to enter a mammal's 408 blood vessel 409. The nanogel 406 can then enter target tissue 414 in which cancerous cells 411 are dispersed amongst healthy cells 410. As shown in FIG. 4B, the drug system 412 is delivered into the cancerous cells 411 specifically though sigma 2 and/or HER-2 receptor delivery, upon which the elevated level of Glutathione (GSH) and Reactive Oxygen Species (ROS) within the cancerous cells 411 will trigger the release of the chemotherapeutic drugs 413 from nanogel 406 in the drug system 412.

Figure 1B:
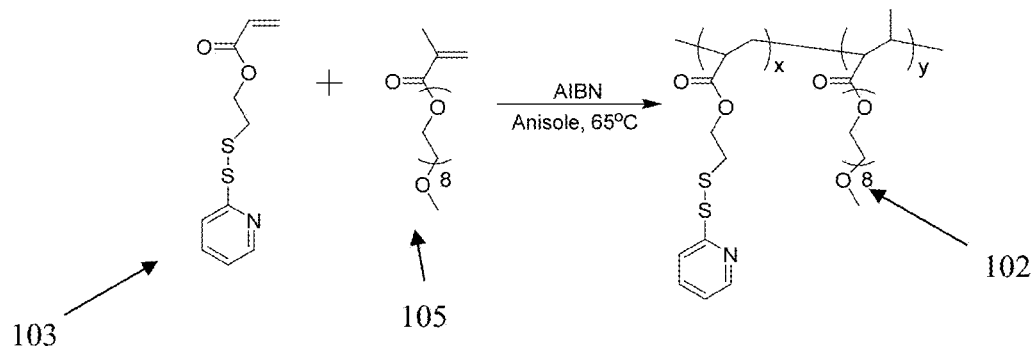
FIG. 1B illustrates the synthesis of polymer PDSA-PEG2.

Referring to FIGS. 1A and 1B, the copolymers, 101 and 102, can be synthesized via a polymeric reaction using Azobisisobutyronitrile (AIBN). Azobisisobutyronitrile is an organic powder that is soluble in organic solvents and can used as a foamer or radical initiator in polymeric reactions, which can be combined with Anisole to initiate a polymeric reaction. In one instance, the copolymer 101 can include an ethyl acrylate 103 and an ethylene oxide 104. In a particular embodiment, the ethyl acrylate 103 can be poly[(2-(pyridin-2-yldisulfanyl) ethyl acrylate) (PDSA) and the ethylene oxide 104 can be polyethylene glycol with a hydroxide group (PEG1). However, it is also to be understood that the ethyl acrylate can also include (pyridine-2-thiol)ethyl acrylate, (pyridine-2-thiol) ethyl methacrylate, ethyl (2-(pyridin-2-yldisulfanyl)ethyl) carbonate, N-(2-(pyridin-2-yldisulfanyl)ethyl) acrylamide, or a combination thereof. In another embodiment, copolymer 102 can be synthesized using an ethyl acrylate 103 and an ethylene glycol 105. In a particular embodiment, the ethyl acrylate 103 can be poly[(2-(pyridin-2-yldisulfanyl) ethyl acrylate) (PDSA) and the ethylene oxide 105 can be polyethylene glycol with a methyl group (PEG2). It is understood that the copolymer 101 or 102 can be made of any suitable ethyl acrylate 103 or ethylene oxide 104 or 105, so long as the copolymer is water soluble and can facilitate the transport and release of chemotherapeutic drug agents 413 into cancerous cells 411.

Figure 2A:
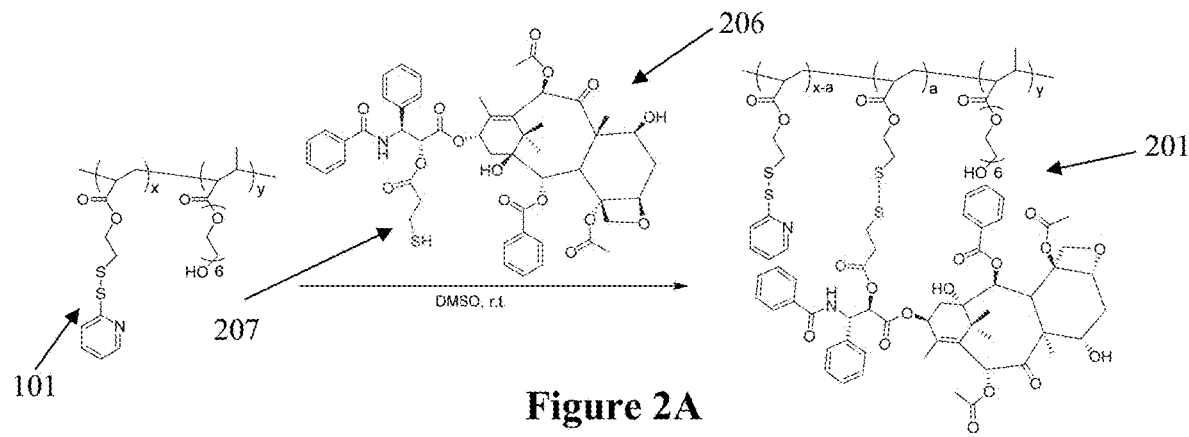
FIG. 2A illustrates the synthesis of polymer PDSA-PEG-PTX.
Figure 2B:
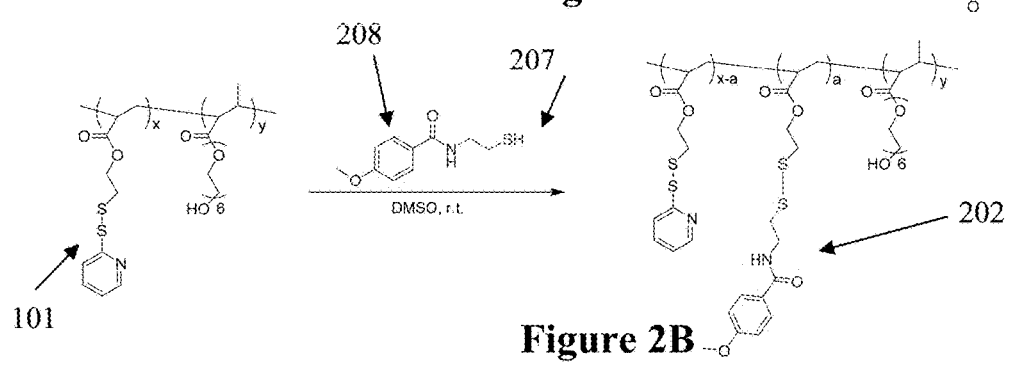
FIG. 2B illustrates the synthesis of polymer PDSA-PEG-MBA.
Figure 2C:
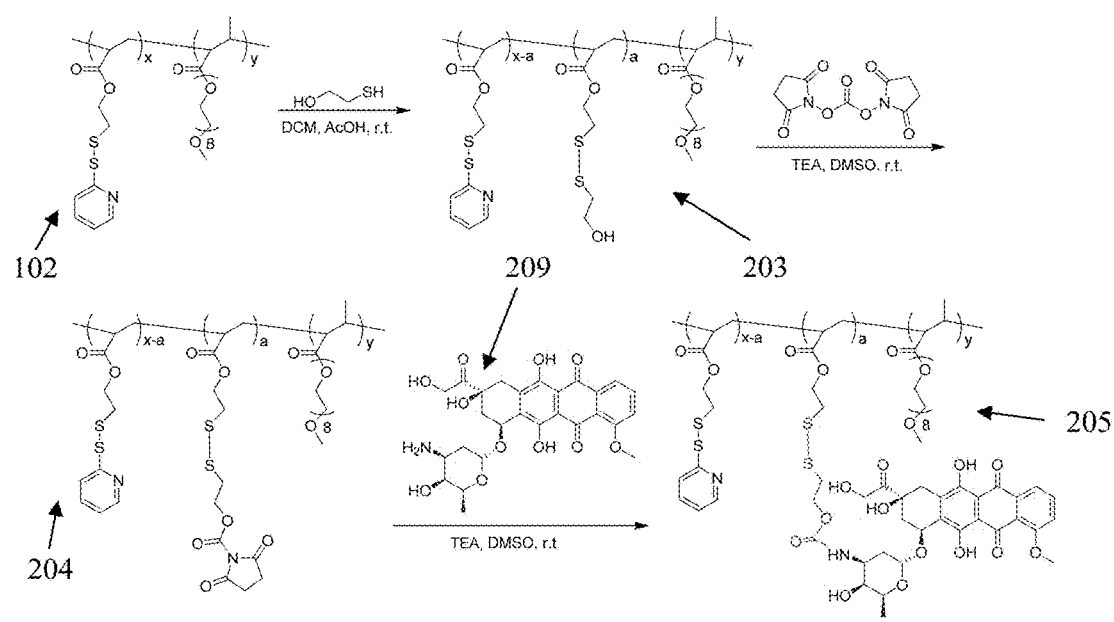
FIG. 2C illustrates the synthesis of polymer PDSA-PEG-DOX.

Referring to FIGS. 2A-2C, the synthetic drug routes for the conjugation of a first chemotherapeutic agent such as a terpene-derived chemotherapeutic agent 206, a second chemotherapeutic agent such as a bacterially-derived chemotherapeutic agent 209, and a benzamide 208 onto copolymer 101 or copolymer 102 are described. FIG. 2A describes the pathway of a terpene-derived chemotherapeutic agent 206 to be conjugated onto copolymer 101 to create a polymeric carrier 201. The reaction includes the use of a traceless linker 207 and disulfide bonds to conjugate the terpene-derived chemotherapeutic agent 206 onto copolymer 101 in the presence of dimethyl sulfoxide (DMSO). In one embodiment, the terpene-derived chemotherapeutic agent can include a taxane. Taxanes are class of diterpenes derived from plants of the genus *Taxus* (yews) and are commonly used as chemotherapeutic agents for the treatment of cancer. Examples of suitable taxanes for cancer treatment include paclitaxel and docetaxel. In a particular embodiment, the taxane conjugated in this reaction can comprise paclitaxel (PTX). Traceless linkers 207 are a strategy used to facilitate the release of chemotherapeutic drugs 413 into cancerous cells 411 such that the drugs can reach the targeted site at maximum potency by allowing for the drug to not be modified with a functional group. The linkers can be conjugated onto copolymer 101 or copolymer 102 when conjugating on a terpene-derived chemotherapeutic agent 206, a bacterially-derived chemotherapeutic agent 209, or a benzamide 208 with the help of disulfide bonds. When cleaved at the cancerous site, the traceless linkers 207 break, allowing for the chemotherapeutic agents to be released in their original form. In one particular embodiment, the traceless linkers 207 can be a thiol group.

FIG. 2B provides an example of the pathway of a benzamide 208 to be conjugated onto copolymer 101 with a traceless linker 207 to create a polymeric carrier 202 in the presence of DMSO. Benzamides, and their common derivatives, can be used to target sigma 2 receptors within a target cell, a sigma receptor subtype that is highly expressed in breast, ovarian, lung, brain, bladder, and colon cancers. In one embodiment, the benzamide 208 can comprise 4-methoxybenzamide. FIG. 2C provides an example of the conjugation pathway of a bacterially-derived chemotherapeutic agent 209 onto a copolymer 102. The reaction can comprise the creation of an intermediate polymer 203 in the presence of dichloromethane (DCM) and acetic acid (AcOH), which is then used to create a secondary intermediate polymer 204 in the presence of TEA and DMSO, and finally bonding the bacterially-derived chemotherapeutic agent 209 to make a polymeric carrier 205 in the presence of TEA and DMSO. Further, the bacterially-derived chemotherapeutic agent 209 can be an anthracycline. Anthracyclines are a class of chemotherapy drugs that are extracted from Streptomyces bacterium. Examples of suitable anthracyclines contemplated by the present invention include doxorubicin, daunorubicin, epirubicin, and idarubicin. In one particular embodiment, the chemotherapeutic agent 110 can be doxorubicin. In one embodiment, the process may be a 3-step reaction, requiring the creation of an intermediate polymer 203 and a secondary intermediate polymer 204.

Figure 3A:
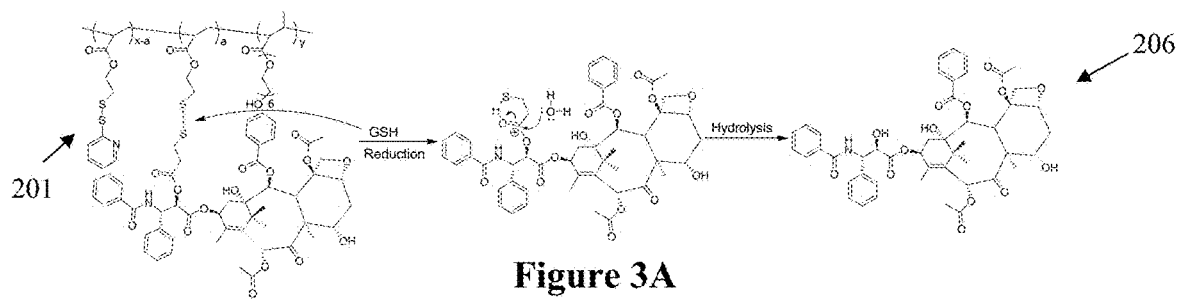
FIG. 3A illustrates a drug release mechanism of the redox dual-responsive disulfide bond, specifically the mechanism of GSH-triggered PTX release from PPP.
Figure 3B:
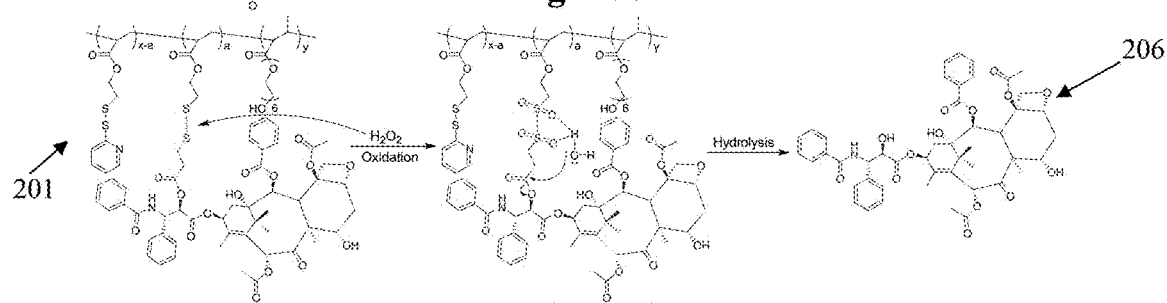
FIG. 3B illustrates a drug release mechanism of the redox dual-responsive disulfide bond, specifically the mechanism of $H_2O_2$-triggered PTX release from PPP.
Figure 3C:
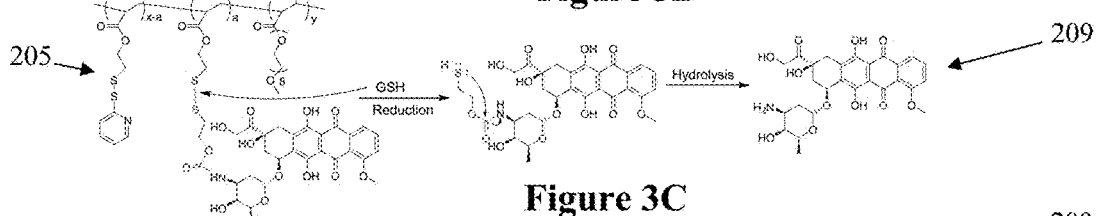
FIG. 3C illustrates a drug release mechanism of the redox dual-responsive disulfide bond, specifically the mechanism of GSH-triggered DOX release from PPP.
Figure 3D:
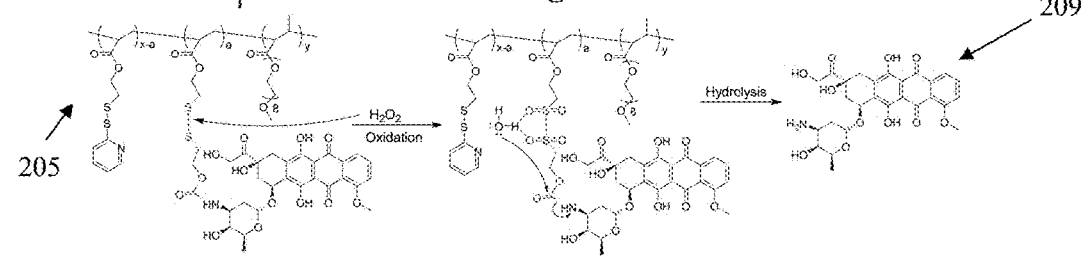
FIG. 3D illustrates a drug release mechanism of the redox dual-responsive disulfide bond, specifically the mechanism of $H_2O_2$-triggered DOX release from PPP.

FIGS. 3A-3D provide an example of drug release pathways for polymeric carrier 201 and polymeric carrier 205 to release chemotherapeutic agents 413. Elevated levels of reactive oxygen species (ROS) and glutathione (GSH) levels are two common hallmarks of cancer. Since most anti-cancer drugs show tempered therapeutic efficacy post modification, it is crucial to ensure that the conjugated drug can be released in its original form at the site of action. To achieve this, a traceless release design was introduced so that the conjugated terpene-derived chemotherapeutic agent 206 and bacterially-derived chemotherapeutic agent 209 will be released upon exposure to elevated levels of ROS and GSH. FIGS. 3A and 3B show an example of the cleavage of a polymeric carrier 201 to release a terpene-derived chemotherapeutic agent 206 by GSH (FIG. 3A) and an ROS, which can comprise $H_2O_2$ (FIG. 3B). FIGS. 3C and 3D show an example of the cleavage of a polymeric carrier 205 to release a bacterially-derived chemotherapeutic agent 209 by GSH (FIG. 3C) and a ROS, which can comprise $H_2O_2$ (FIG. 3D).

It has been reported that HER2, or so called ErbB2 receptors, and sigma 2 receptors are overexpressed in many cancers, including ovarian cancer, breast cancer, and head and neck cancer. In one embodiment, a benzamide 208 (e.g., a first targeting ligand) and an affinity ligand 415 (e.g., a second targeting ligand) can be conjugated onto the nanogel 406 to target sigma 2 receptors and HER2 receptors, respectively. In a particular embodiment, the affinity ligand 415 can be an AFFIBODY® molecule. AFFIBODY® molecules are small, robust proteins engineered to bind to a large number of target proteins with high affinity that are considered part of the family of antibody mimetics for targeted therapy. In one particular embodiment, the AFFIBODY® molecule can comprise Anti-ErbB2 AFFIBODY® molecule. Anti-ErbB2 AFFIBODY® molecules can specifically target HER2, alternatively called ErbB2, receptors that are overexpressed in cancerous cells.

By inclusion of the various components above, wherein such components have been found to act synergistically, the present invention contemplates a targeted nanogel 406 based on a non-toxic dose of a combination of a first chemotherapeutic agent, such as a terpene-derived chemotherapeutic agent 206, and a second chemotherapeutic agent, such as a bacterially-derived chemotherapeutic agent 209, carried by a nanogel 406 comprising both copolymer 101 and copolymer 102 for the treatment of cancer, such as ovarian cancer. In one particular embodiment, the nanogel 406 can include a PDSA-PEG polymer carrier, paclitaxel (PTX), doxorubicin (DOX), 4-methoxybenzamide (MBA), and Anti-ErbB2 AFFIBODY® (AEB) molecule. The inclusion of these components into a singular nanogel shall herein be abbreviated PPPDMA, where PPPDMA can include any variants of the components listed above. Further, the use of the terms paclitaxel (PTX), 4-methoxybenzamide (MBA), doxorubicin (DOX), Anti-ErbB2 (AEB), and PDSA-PEG are meant to include both these particular embodiments and any suitable variants.

It has been found that a combination of both PTX and DOX chemotherapeutic agents produces a synergistic effect in killing cancer cells. Thus, a nano-cocktail containing both PTX and DOX (PPPD) was fabricated by dissolving PDSA-PEG-PTX and PDSA-PEG-DOX polymers in dimethyl sulfoxide (DMSO) and dialyzing against water. By controlling the ratio of PTX to DOX, the synergistic killing effect on cancer cells can be optimized. For instance, the molar ratio of terpene-derived chemotherapeutic agent 206 to a bacterially-derived chemotherapeutic agent 209, as contemplated by the present invention, can range from about 1:1 to about 1:1000, such as from about 1:5 to about 1:30, such as from about 1:10 to about 1:25. In one particular embodiment, the molar ratio can range from about 1:15 to about 1:20.

In addition, although PTX and DOX have been described above as examples of the first chemotherapeutic agent and the second chemotherapeutic agent of the present invention, it is to be understood that other chemotherapeutic agents are also contemplated, so long as the first chemotherapeutic agent is different from the second therapeutic agent. For instance, the first chemotherapeutic agent and the second chemotherapeutic agent can be selected from the group consisting of doxorubicin, paclitaxel, daunorubicin, valrubicin, triptolide, epirubicin, idarubicin, docetaxel, cisplatin, carboplatin, oxaliplatin, camptothecin, vincristine, vinblastine, 5-fluorouracil(5-FU), mitomycin, cyclophosphamide, methotrexate, mitoxantrone, topotecan, capecitabine, doxifluridine, irinotecan, tegafur, chlorambucil, belotecan, anastrozole, tamoxifen, GLEEVEC® (imatinib), floxuridine, leuprolide, flutamide, zoledronate, streptozocin, vinorelbine, hydroxyurea, retinoic acid, mechlorethamine, busulfan, prednisone, testosterone, aspirin, salicylates, ibuprofen, naproxen, fenoprofen, indomethacin, phenyltazone, mechlorethamine, dexamethasone, prednisolone, celecoxib, valdecoxib, nimesulide, cortisone, corticosteroid, gemcitabine, cedrol, or a combination thereof.

Moreover, it should also be understood that the first targeting ligand and the second targeting ligand can be selected from the group consisting of 4-methoxybenzamide, Anti-ErbB2 AFFIBODY® molecule, Anti-EGFR AFFIBODY® molecule, folic acid, β-d-glucose, Asn-Gly-Arg peptide, Angiopep2, HERCEPTIN®, transferrin, arginine-glycine-aspartate peptide, lactobionic acid, or a combination thereof, so long as the first targeting ligand and the second targeting ligand are different.

Further, by controlling the various concentrations of individual components of the nanogel 406, the size of the nanogel 406 can be controlled to optimize the effect of the nanogel on the cancer cells. In one embodiment, the nanogel can exhibit a spherical morphology with a diameter of about 50 nanometers to about 150 nanometers, such as from about 60 nanometers to about 140 nanometers, such as from about 80 nanometers to about 125 nanometers. It was found that this sizing has allowed for the nanogel 406 to have a surface charge that increases stability during blood circulation. This surface charge can range from about −1 millivolts to about −50 millivolts, such as from about −5 millivolts to about −30 millivolts, such as from about −10 millivolts to about −20 millivolts.

As shown in the following example, the polymeric carrier is conjugated with various components to effectively inhibit the proliferation of metastatic cancer cells. Furthermore, the use of PTX/DOX dual drug conjugate can significantly increase the effect of both drugs while not inducing renal or toxicity responses typically associated with using PTX and DOX without a polymeric carrier. Moreover, the implementation of a traceless linking strategy can allow for drug deliveries of chemotherapeutic agents that do not decrease in potency while also inhibiting a toxicity response.

The various components of the total nanogel, PDSA-PEG-PTX-DOX-MBA-AEB (PPPDMA), can also be combined in various ways for both reference and testing. For instance, the nanogel PDSA-PEG-PTX (PPP) can be created to test the elution time of paclitaxel. In another embodiment, the nanogel PDSA-PEG-DOX (PPD) can be created to test the elution time of doxorubicin specifically.

The present invention may be better understood with reference to the following example.

EXAMPLE

1. Materials and Methods 1.1. Synthesis of PDSA-PEG1 and PDSA-PEG2

The polymers, PDSA-PEG1 and PDSA-PEG2, were synthesized through free radical polymerization as reported previously. In brief, 482 mg (2.0 mmol) PDSA and 2.0 mmol PEG derivatives (720 mg PEGMA for PDSA-PEG1, 960 mg PEGMMA for PDSA-PEG2) were dissolved into 10 mL anisole in a 50 mL round-bottom flask and degassed with nitrogen for 30 minutes at room temperature. After that, a degassed solution of AIBN (32.8 mg, 0.2 mmol) in 1 mL anisole was added dropwise into the reaction mixture. Then the flask was immersed in an oil bath maintained at 65° C. and stirred for 24 hours in the dark. Following the reactions, the resulting polymers were collected by precipitation with ice-cold diethyl ether. For further purification, the collected polymers were dissolved in DCM and then precipitated with ice-cold diethyl ether for three times. The purified polymers were dried under vacuum in the dark until the solvents were completely removed. The structural compositions of PDSA-PEG1 and PDSA-PEG2 were analyzed by NMR using $CDCl_3$ as the solvent. The average molecular weight of the polymers was determined by gel permeation chromatography (GPC).

1.2. Synthesis of PDSA-PEG-PTX (PPP)

The polymer PDSA-PEG-PTX was synthesized through a thiol-disulfide exchange reaction between the thiol group of PTX-SH and the disulfide bond of PDSA-PEG1. Typically, 18 mg PDSA-PEG1 was dissolved in 500 µL DMSO, followed by dropwise addition of 14 mg PTX-SH in 200 µL DMSO. The reaction mixture was stirred at room temperature overnight in the dark and then dialyzed towards DMSO using SPECTRA/POR® dialysis tube (MWCO: 8 kDa) to get rid of unreacted PTX-SH. The final product was obtained from precipitation with ice-cold diethyl ether. Then the polymer was dissolved into DCM, precipitated with ice-cold diethyl ether twice to eliminate DMSO residue, and dried under vacuum in the dark for 48 hours. The chemical structure of PDSA-PEG-PTX was confirmed by $^1$H NMR and the content of PTX in PDSA-PEG-PTX was measured with high performance liquid chromatography (HPLC).

1.3. Synthesis of PDSA-PEG-MBA (PPPM)

PDSA-PEG-MBA was synthesized in the same way as the synthesis of PDSA-PEG-PTX. 3.2 mg MBA-SH in 200 µL DMSO was added to 500 µL DMSO solution of 18 mg PDSA-PEG1 drop by drop. The resulted solution was kept at room temperature in the dark overnight, followed by dialysis against DMSO with SPECTRA/POR® dialysis tube (MWCO: 1 kDa) to remove unreacted MBA-SH. The desired polymer was collected from precipitation with ice-cold diethyl ether and further purified by precipitating from DCM solution with ice-cold diethyl ether twice. After being dried in vacuo for 48 hours in the dark, the polymer PDSA-PEG-MBA was analyzed with $^1$H NMR to confirm its chemical structure, and its content of MBA was determined by HPLC.

1.4. Synthesis of PDSA-PEG-BME

The intermediate polymer PDSA-PEG-BME was prepared via thiol-disulfide exchange reaction between 2-mercaptoethanol (BME) and polymer PDSA-PEG2. PDSA-PEG2 (22 mg) was dissolved in 500 µL DCM with a catalytic amount of glacial acetic acid. While vigorously stirring, 1.6 mg BME in 200 µL DCM was added dropwise. The reaction was kept stirring overnight in the dark at room temperature. Then the targeting product was precipitated with ice-cold diethyl ether and further purified through precipitation with DCM and ice-cold diethyl ether for two more times. The polymer PDSA-PEG-BME was dried under vacuum in the dark for 48 hours, and its structural composition was confirmed by $^1$H NMR.

1.5. Synthesis of PDSA-PEG-DSC

The free hydroxyl group of PDSA-PEG-BME was replaced by N-succinimidyl carbonate group to produce PDSA-PEG-DSC. PDSA-PEG-BME (20 mg) and 7.7 mg N,N'-disuccinimidyl carbonate (DSC) were dissolved in 500 µL DMSO. Then 8.4 µL TEA was added and the reaction solution was stirred overnight at room temperature in the dark. The unconjugated DSC was removed by dialyzing the reaction mixture towards DMSO using SPECTRA/POR® dialysis tube (MWCO: 8 kDa). The desired product PDSA-PEG-DSC was gathered by precipitation with ice-cold diethyl ether. Further removal of DMSO residue was performed twice via DCM/ice-cold diethyl ether precipitation. After in vacuo dryness in the dark for 48 hours, the polymer was analyzed by $^1$H NMR to verify its chemical structure.

1.6. Synthesis of PDSA-PEG-DOX (PPD)

The anticancer drug DOX was conjugated to the polymer through a reaction between the newly introduced succinimidyl group of PDSA-PEG-DSC and the amino group of DOX. To a solution of 20 mg PDSA-PEG-DSC in 500 µL DMSO, 16.3 mg DOX was added, followed by the addition of 10 µL TEA. The resulting reaction mixture was kept in the dark, stirring at room temperature for 24 hours. SPECTRA/POR® dialysis tube (MWCO: 8 kDa) was utilized to remove unreacted free DOX through dialysis against DMSO. Then the purified polymer solution was dialyzed towards deionized water to exchange DMSO into water. The final polymer PDSA-PEG-DOX was collected through lyophilization in the dark. The molecular structure of PDSA-PEG-DOX was confirmed by $^1$H NMR and the content of DOX in PDSA-PEG-DOX was determined with HPLC.

1.7. Fabrication of Nanogels

Generally, 0.3 mg TCEP in 20 µL DMSO was added to a solution of 10 mg polymer (or a mixture of different polymers) in 0.5 mL DMSO upon vigorous stirring. After equilibration for 15 minutes, the resulted mixture was dropped into 5 mL deionized water under robust stirring and maintained stirring overnight. Following that, the polymer nanogels were dialyzed in SPECTRA/POR® dialysis tube (MWCO: 8 kDa) against PBS (pH 7.4) for 24 hours to eliminate small molecules. At last, the nanogels were filtered through 0.45 µm syringe filters and stored at 4° C. The particle size, size distribution (polydispersity index, PDI), and surface charge of the nanogels were determined by dynamic light scattering (DLS) and zeta potential measurement, recorded on ZETASIZER® (ZETASIZER® NANO® ZS, Malvern Instruments Ltd., Malvern, UK). The morphology of polymer nanogels was observed using Hitachi HT7800 transmission electron microscopy (TEM, Hitachi High-Technologies Corporation, Tokyo, Japan). For the preparation of a series of MBA functionalized PPP nanogel, PPPM (PPPM1, PPPM2, PPPM3, and PPPM4), mixtures of different ratios of PDSA-PEG-PTX:PDSA-PEG-MBA (w/w) at 9:1, 8:2, 6:4, and 5:5 were used, respectively. The size distribution (Dp and PDI), and zeta potential data of all the PPPM series of polymer nanogels are summarized in Table 1.

1.8. Conjugation of AEB

The tumor-targeting Anti-ErbB2 AFFIBODY® (AEB) molecule, a thiol-containing AFFIBODY® molecule, was conjugated to polymer nanogels by thiol-disulfide exchange reaction. The above-prepared PPD or PPPD nanogels dispersed in PBS (pH 7.4) were mixed with different amount of AEB dissolved in PBS (pH 7.4) to prepare AEB-conjugated PPDSA or PPPDSA nanogels, respectively. The resulted reaction mixtures were stirred at 4° C. overnight. The conjugation of AEB was monitored by measuring the release of 2-pyridinethione with UV-Vis spectrophotometer (DU 650 Spectrophotometer, Beckman Coulter, USA) at 375 nm (molar absorption coefficient: 8080 $M^{-1}$ $cm^{-1}$). The unconjugated free AEB, which has a molecular weight of 6 kDa, was removed from the nanogel system by centrifuging with AMICON® Ultra centrifugal filter (MWCO: 30 kDa). The AEB-decorated nanogels were collected and dispersed into PBS (pH 7.4) and then stored at 4° C. for future use. For the preparation of a series of AEB AFFIBODY® molecule functionalized PPD nanogel, PPDSA (PPDSA1, PPDSA2, PPDSA3, and PPDSA4), mixtures of different ratios of PPD:AEB (w/w) at 640:1, 320:1, 160:1, and 100:1 were used, respectively. The size distribution (Dp and PDI), and zeta potential data of all the PPDSA series of polymer nanogels are summarized in Table 3.

1.9. Drug Release

The release profiles of PTX and DOX from PPP and PPD nanogels were investigated at 37° C. with different buffer solutions (containing 1% TWEEN®80, m/v) as release media, including acetate buffer (pH 5.0), PBS buffer (pH 7.4), PBS with 10% FBS (pH 7.4), PBS with 10 mM GSH (pH 7.4), and PBS with 10 mM $H_2O_2$ (pH 7.4). Nanogels (equivalent to 200 nmol PTX/DOX) suspended in certain release medium (without TWEEN®80) were instantly sealed into SPECTRA/POR® dialysis tube (MWCO: 8 kDa) and immediately immersed into 100 mL pre-warmed respective release medium. At predetermined time points, 10 mL release medium outside of the dialysis tube was sampled and same amount of fresh release medium was replaced to make the total volume of the release system constant. The sample was lyophilized and then dissolved into acetonitrile for HPLC analysis.

1.10. Serum Stability

The hydrodynamic stability of the nanogels were monitored by DLS. Nanogels were first dispersed in PBS buffer (pH 7.4) and PBS buffer with 10% FBS (pH 7.4), and then incubated at 37° C. for up to 8 days. The size of the nanogels were determined with DLS at predetermined time points.

1.11. Cell Culture

Human ovarian cancer cells, SKOV-3 and SKOV-3/Luc cells, were cultured in GIBCO™ DMEM supplemented with 10% FBS, 100 units/mL penicillin, and 100 µg/mL streptomycin at 37° C. in 75 mL culture flasks under a humidified atmosphere of 5% $CO_2$. Cells were sub-cultured when the cell confluence reached ~80%.

1.12. Cytotoxicity Assay

The anticancer activities of polymer nanogels against SKOV-3 cells were evaluated by MTT assay. Cells were seeded in 96-well plates at a density of 5,000 cells/well for 24 hours prior to the test at 37° C. with 5% $CO_2$. Then the cells were treated with varying concentrations of PTX/DOX or polymer nanogels in fresh medium and further incubated for 72 hours. In the control group, cells were allowed to grow without any treatment. After that, the medium was replaced with 100 µL fresh medium containing MTT reagent (final concentration 1 mg/mL) and cells were further incubated for 4 hours. The purple MTT crystal was dissolved with 100 µL MTT stop solution and the optical density at 595 nm was recorded on a microplate reader (ELx808™ Absorbance Microplace Reader, Bio-Tech Instrument, Inc.).

1.13. Confocal Microscopy

The cellular uptake of poly-nano-prodrugs was qualitatively examined by confocal laser scanning microscopy (CLSM) with SKOV-3 cells. Cells were seeded in 35 $mm^2$ petri dish with a glass window at a density of 200,000 cells/dish for 24 hours at 37° C. with 5% $CO_2$. Then the cells were washed with PBS (pH 7.4) and incubated with free DOX or DOX-contained prodrugs with equivalent concentration of 2 µM DOX for 3 hours. Cells without any incubation were utilized as control. All cells were subsequently washed three times with PBS and fixed with paraformaldehyde (4% in PBS) for 10 minutes at room temperature. Cells were washed with PBS again for three times after the removal of paraformaldehyde, and the nuclei of cells were stained with Hoechst 33342 (final concentration 1 µg/mL) for 10 minutes. At last, cells were washed three times with PBS and then imaged under a confocal microscope (LSM 700, Carl-Zeiss Inc.).

1.14. Flow Cytometry

The uptake of prodrugs by SKOV-3 cells was further quantitatively determined by flow cytometry. Cells were seeded in 6-well plates at a density of 300,000 cells/well for 24 hours at 37° C. with 5% $CO_2$. Then the cells were washed with PBS (pH 7.4) and incubated with free DOX or DOX-contained poly-nano-prodrugs with equivalent concentration of 1 µM DOX for 3 hours. Cells with no incubation were utilized as control. After that, the cells were washed with PBS, trypsinized with trypsin-EDTA, and collected through centrifuging (2000 rpm, 3 minutes). Cells were suspended into PBS and then centrifuged for two more times. Finally, collected cells were re-suspended into PBS for analysis. Intracellular fluorescence intensity was quantified by flow cytometer (BD ACCURI™ C6, BD Biosciences) at $\lambda_{ex}$ 488 and $\lambda_{em}$ 560 nm.

1.15. Animal Model

All animal experiments were conducted in accordance with NIH regulations and approved by the Institutional Animal Care and Use Committee of the University of South Carolina. A mouse model of intraperitoneal (IP) ovarian metastatic tumor was established. In brief, SKOV-3/Luc cells, a luciferase expressing cell line derived from SKOV-3, were cultured in DMEM culture medium. 2,000,000 cells were suspended in 200 µL DMEM and intraperitoneally injected to a female nude mouse (8-10 weeks old, ~20*g*, Jackson Laboratories). The tumor burdens were monitored with a whole body imaging system weekly and the animals were observed for body weight change and signs of pain every other day throughout the duration of experiments.

1.16. Whole Body Imaging

The tumor growth of mice was monitored using a non-invasive IVIS® Lumina III whole body imaging system (PerkinElmer Inc., Waltham, USA). The tumor-bearing nude mice were first anesthetized by 2% isoflurane and then injected intraperitoneally with 200 µL D-luciferin (15 mg/mL in PBS). After approximately 15 minutes, the whole body of mice was imaged to record the bioluminescence emitted from SKOV-3/Luc tumors. The imaging time was optimized and all images were collected under identical system settings. The images were analyzed by LIVING IMAGE® software and the intensity of recorded bioluminescence signals was quantified in radiance.

1.17. In Vivo Biodistribution

Three weeks after the inoculation of SKOV-3/Luc cells, the tumor-bearing mice were administered with various nanogels by intraperitoneal injection at a dose of 1 mg/kg equivalent to DOX. PBS (pH 7.4) was used as control. Mice were sacrificed 6 hours post-injection, and the organs and tumors were collected for imaging. The fluorescence was recorded ex vivo with the IVIS® Lumina III whole body imaging system.

1.18. Anti-Tumor Efficacy

After inoculation with SKOV-3/Luc cells for two weeks, the tumor-bearing mice were randomly assigned into six groups (n=5 for each group) and were intraperitoneally administrated with PTX+DOX or nanogels at a dose of 1 mg/kg equivalent to PTX and 12 mg/kg equivalent to DOX. Free PTX was administrated in the formulation of TAXOL® (paclitaxel). PBS (pH 7.4) was used as control. Mice were marked and weighed prior to treatment. The treatments were given to mice once per week. After six weeks, all mice were sacrificed to harvest the organs and tumors for further analysis.

1.19. Histological Analysis

The collected organs (heart, liver, spleen, and kidney) were fixed in 4% paraformaldehyde solution. Then the fixed organs and tumor tissues were embedded in optimal cutting temperature (OCT) gel, sectioned into ~10 μm, stained with hematoxylin and eosin (H&E), and analyzed under a light microscope. The histology was performed in a blinded fashion.

1.20. Statistical Analysis

All data were processed and demonstrated as means with standard deviations (mean SD). A t-test was utilized to analyze statistical difference between parallel groups. P<0.05 from a two-tailed test was considered statistically significant.

Figure 5:
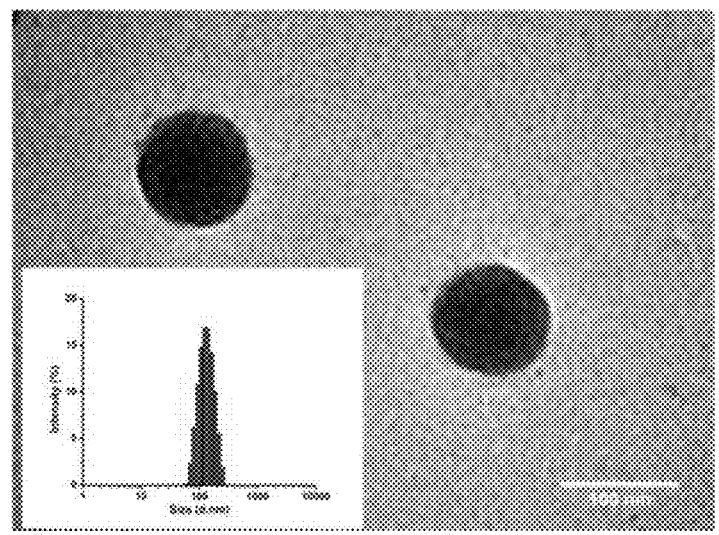
FIG. 5 shows a TEM image and the size distribution spectrum acquired by DLS (insert) of PPDMA nanogels. Scale bar is 100 nm.

2. Results 2.1 Size Characterization of PPPM, PPPD, PPPDM, PPPDSA, and PPPDMA Nanogels Nanoparticle size is an important to factor in determining the behavior of nanogels in drug delivery. The size and morphology of a nanogel affects the interactions and effectiveness of the drug when used on cancer patients. The inventors have determined that the most effective size for treating cancer is from about 80 nanometers to about 125 nanometers, especially about 118.7 nanometers. FIG. 5 is a representation of a Trans-Electron Microscopy (TEM) image of the nanoparticles along with a Dynamic Light Scattering (DLS) size distribution. TEM revealed that the size of the PPPDMA is about 100 nm with a spherical shape, which matches well with the size of 118.7 nm achieved through dynamic light scattering (DLS) (FIG. 5).

Figure 6:
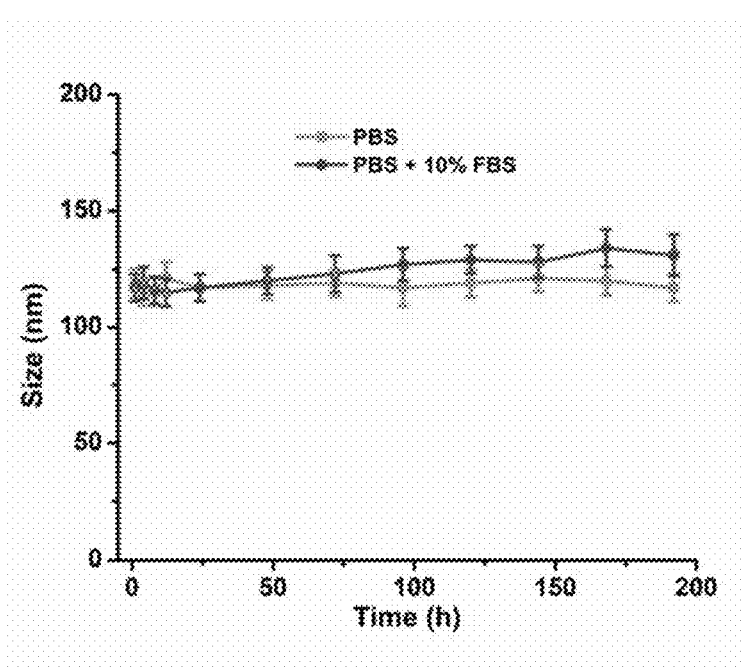
FIG. 6 shows size change curves of PPPDMA in PBS and PBS supplemented with 10% FBS.

Further analysis of the nanogels show strong stability in solution as seen by the relative size stability over the course of 8 days in FIG. 6, suggesting the good biocompatibility of PPPDMA with blood components during circulation, which may be attributed to its negative surface charge. The relative size and zeta potentials of each tested nanogel are displayed below. It was found that the surface charge of the nanogels is −18.5 mV, suggesting a good stability during blood circulation. Table 1 shows the values of 4 PDSA-PEG-PTX-MBA (PPPM) nanogels. The second column is the molar ratio of PPP to PPM within each PPPM nanogel. Column 3 represents the size of the nanogel, column 4 shows the polydispersity index (PDI), and column 5 the zeta potential. The PDI is a measure of the heterogeneity of sizes of molecules or particles in a mixture. The low PDI values indicate a similar size distribution amongst particles in the nanogel. Zeta potential is the potential difference between the dispersion medium and the stationary layer of fluid attached to the dispersed particle. Zeta potential values indicate an incipient stability for each nanogel. Table 2 shows the values of PDSA-PEG-DOX-AEB (PPDA) nanogels. Column 2 shows the molar ratio of PDD to AEB within each tested nanogel. Table 3 shows comparative values of various nanogels. The efficacy of the stated size of the PPPDMA nanogel will become apparent in the following results.

TABLE 1

The size, distribution (PDI) and zeta potential data of PPPM nanogels.

| Polymer nanogels | PDSA-PEG-PTX: PDSA-PEG-MBA (w/w) | Size (nm) | PDI | Zeta potential (mV) |
| --- | --- | --- | --- | --- |
| PPPM1 | 9:1 | 62.8 | 0.147 | −15.1 |
| PPPM2 | 8:2 | 63.9 | 0.131 | −16.4 |
| PPPM3 | 6:4 | 65.7 | 0.122 | −14.3 |
| PPPM4 | 5:5 | 66.1 | 0.158 | −16.1 |

TABLE 2

The size, distribution (PDI), and zeta potential data of PPDA nanogels.

| Polymer nanogels | PDD: AEB (w/w) | Size (nm) | PDI | Zeta potential (mV) |
| --- | --- | --- | --- | --- |
| PPDA1 | 640:1 | 151.5 | 0.078 | −17.6 |
| PPDA2 | 320:1 | 158.6 | 0.077 | −14.9 |
| PPDA3 | 160:1 | 163.9 | 0.102 | −11.8 |
| PPDA4 | 100:1 | 167.2 | 0.111 | −5.2 |

TABLE 3

The size, distribution (PDI) and zeta potential data of PPPD, PPPDM, PPPDA, and PPPDMA nanogels.

| Polymer nanogels | Size (nm) | PDI | Zeta potential (mV) |
| --- | --- | --- | --- |
| PPPD | 114.9 | 0.147 | −18.5 |
| PPPDM | 112.9 | 0.178 | −16.3 |
| PPPDA | 122.6 | 0.137 | −13.8 |
| PPPDMA | 118.7 | 0.172 | −11.7 |

2.2. Drug Release Profiles of PTX and DOX from a Nanogel

Figure 7:
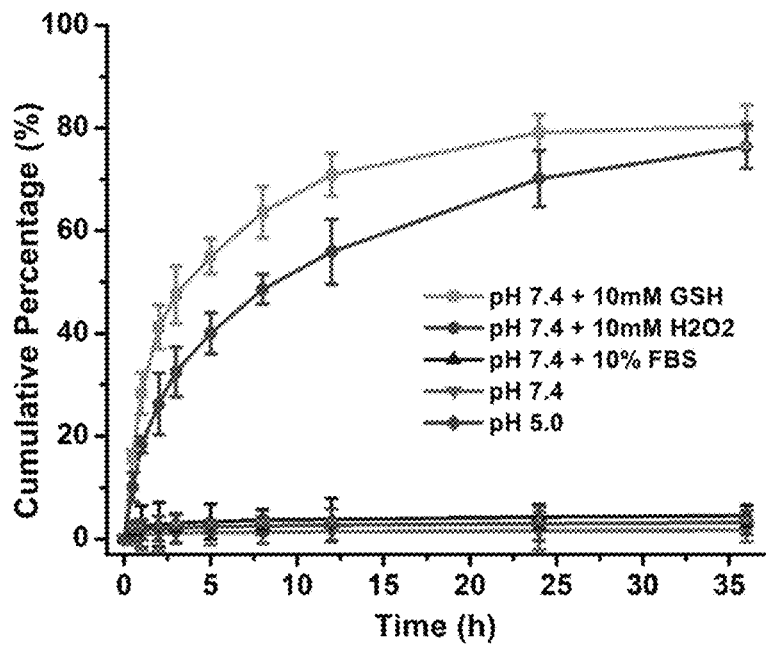
FIG. 7 shows drug release profiles of PTX from PPP nanogels.

To investigate the stability of the drug-loaded nanogel during blood circulation and inside cancer cells, a drug release kinetics study was employed. FIG. 7 shows that only trace amount (<5%) PTX was released in pH 5.0, pH 7.4, or pH 7.4 environment supplemented with 10% serum protein over 36 hours. Interestingly, the addition of 10 mM of GSH or $H_2O_2$ triggered more than 70% or 55% of drug release within 12 hours, respectively. A very similar release pattern was also observed for DOX in FIG. 8. Half maximal inhibitory concentration ($IC_{50}$) elution points for multiple formulations, including free PTX+DOX, are listed in Tables 4-6. $IC_{50}$ is the measure of the potency of a substance in inhibiting a specific biological or biochemical function. It is a quantitative measure of how much inhibitory substance (e.g., a drug) is needed to inhibit, in vivo, a given biological process by 50%.

TABLE 4

The IC50 values of PTX, PPP, and PPPM nanogels.

| Formulations | IC50 (nM) |
|---|---|
| PTX | 30.6 |
| PPP | 97.5 |
| PPPM1 | 55.6 |
| PPPM2 | 35.7 |
| PPPM3 | 34.6 |
| PPPM4 | 35.3 |

TABLE 5

The IC50 values of DOX, PPD, and PPDA nanogels.

| Formulations | IC50 (nM) |
|---|---|
| DOX | 582.1 |
| PPD | 1626.1 |
| PPDA1 | 1038.9 |
| PPDA2 | 772.8 |
| PPDA3 | 341.5 |
| PPDA4 | 345.4 |

TABLE 6

The IC50 values of free PTX+DOX, PPPD, PPPDM, PPPDA, and PPPDMA prodrugs.

| Formulations | IC50 (nM) according to PTX |
|---|---|
| PTX+DOX | 13.1 |
| PPPD | 43.7 |
| PPPDM | 20.9 |
| PPPDA | 10.2 |
| PPPDMA | 6.5 |

2.3. Cell Viability of SKOV-3 Cells after Various Treatments with a Nanogel

Figure 9:
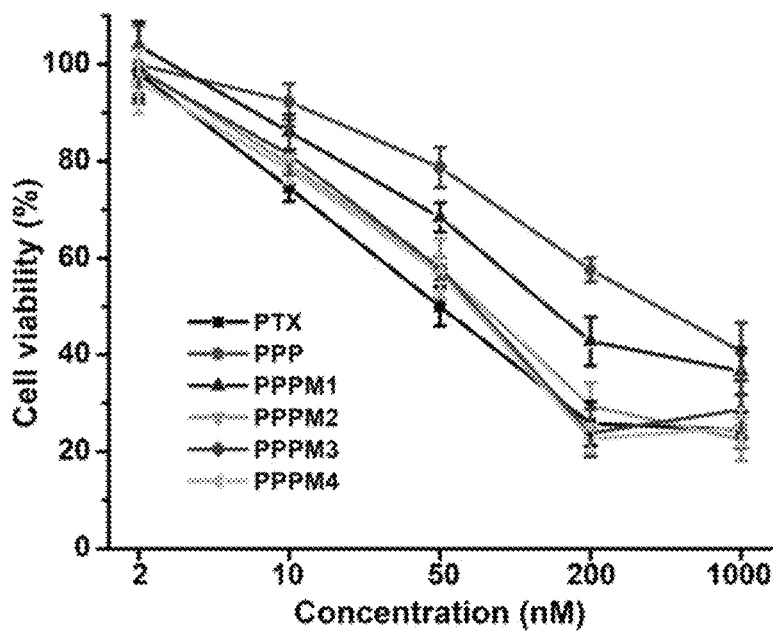
FIG. 9 shows cell viability of SKOV-3 cells after various treatments with PPPM nanogels with different ligand densities for 72 hours, where the data represents the means±SD, n=4.
Figure 10:
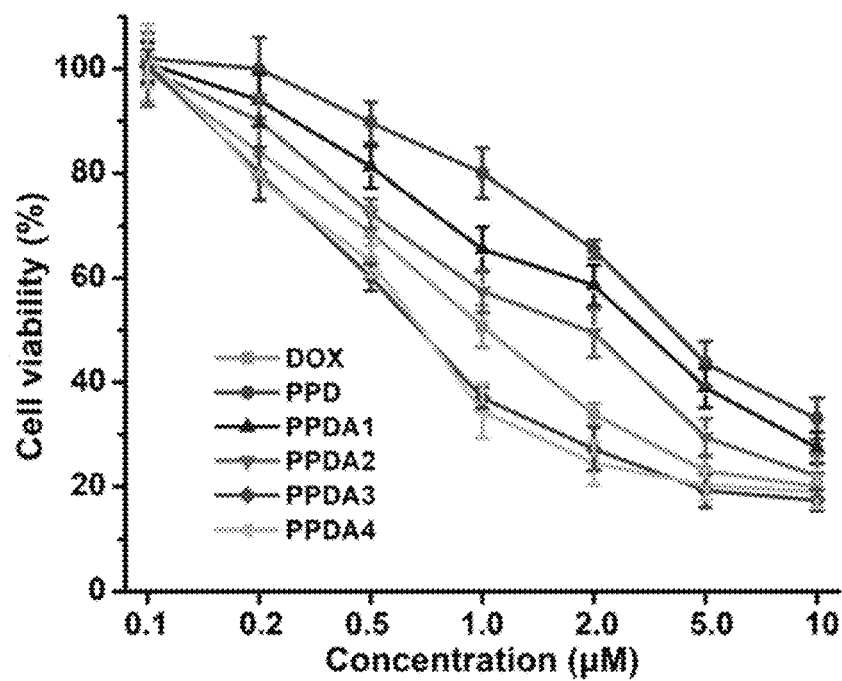
FIG. 10 shows cell viability of SKOV-3 cells after various treatments with PPDSA nanogels with different ligand densities for 72 hours, where the data represents the means±SD, n=4.
Figure 11:
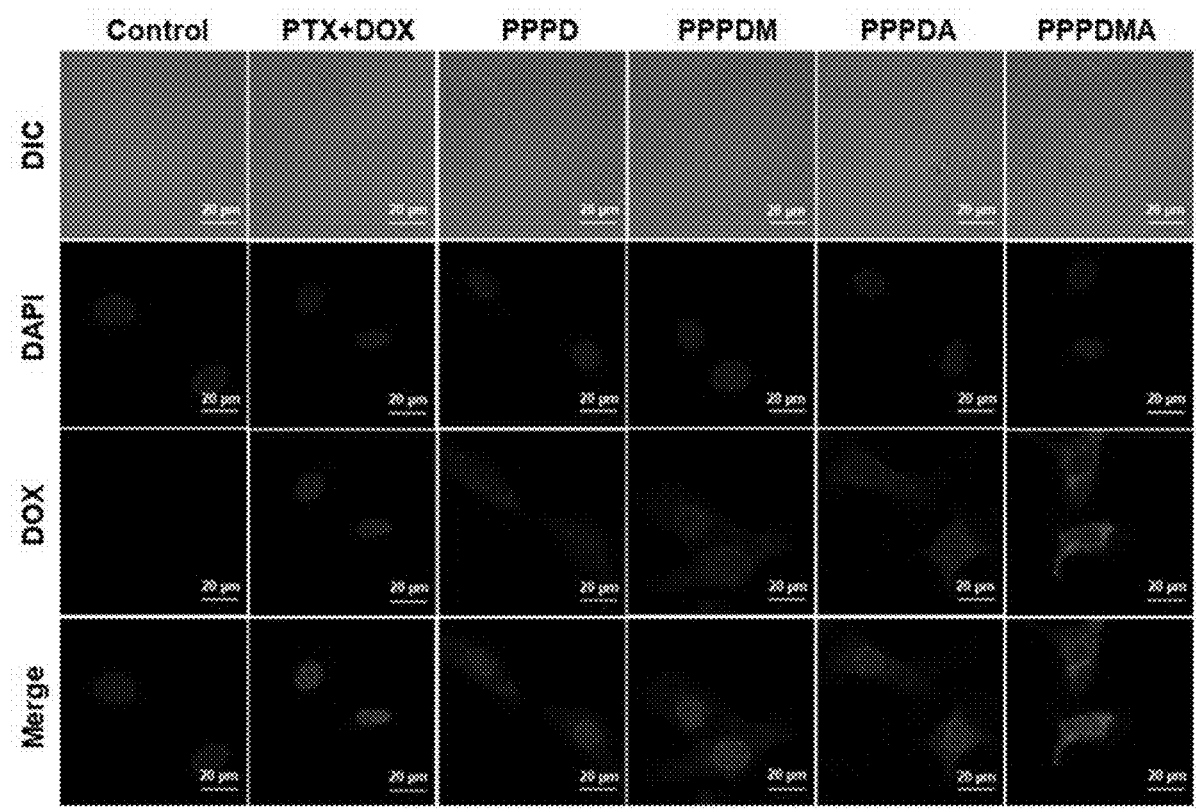
FIG. 11 shows representative CLSM images of SKOV-3 cells after various treatments for 3 hours. Cell nuclei were stained with Hoechst 33342, where the red fluorescence is from DOX and the blue fluorescence is from Hoechst 33342, and where the scale bars are 20 μm.
Figure 12:
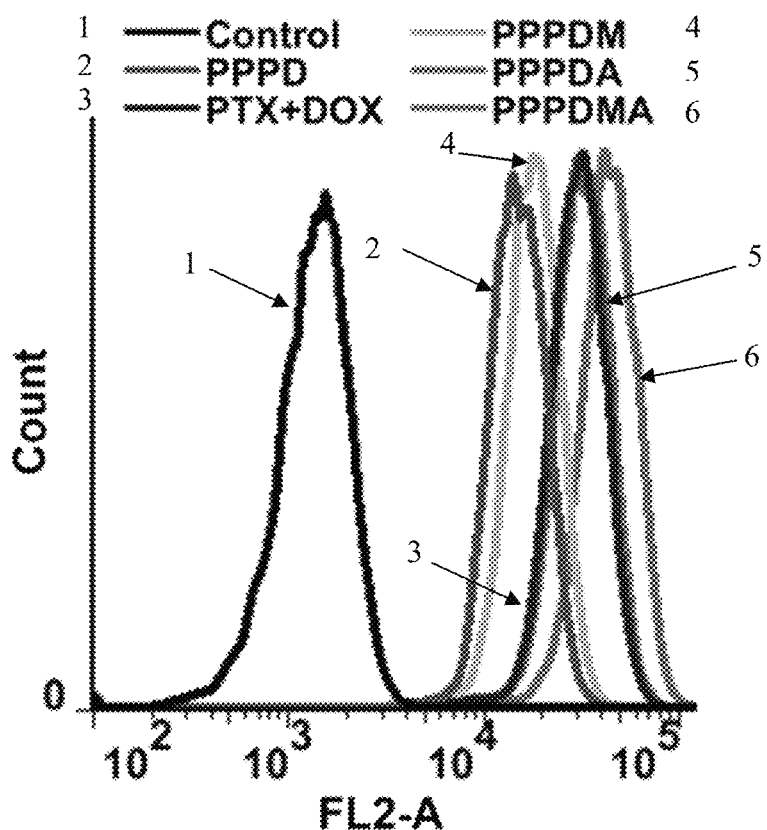
FIG. 12 illustrates flow cytometry analysis of SKOV-3 cells after various treatments for 3 hours.

In vitro experiments were carried out to observe the effects on SKOV-3 ovarian cancer cells. A cell proliferation assay found that the initial increase of ligand density could boost the cell-killing effect of the nanogel in SKOV-3 ovarian cancer cells. However, once the ligand density reached a certain extent, further increase of the ligand density could not yield additional potency, both for MBA and AEB ligands (FIGS. 9 and 10). Confocal microscopy revealed that both MBA and Anti-ErbB2 AFFIBODY® molecule could boost the cellular uptake of PPPD nanogel. As expected, the dual-targeted nanogel, PPPDMA yielded higher DOX fluorescent signal inside its treated cells (FIG. 11) than those treated with its mono-targeted counterparts. Flow cytometry further confirmed that PPPDMA treatment results in the highest cellular uptake efficiency for a PPPD nanogel (FIG. 12).

Figure 13:
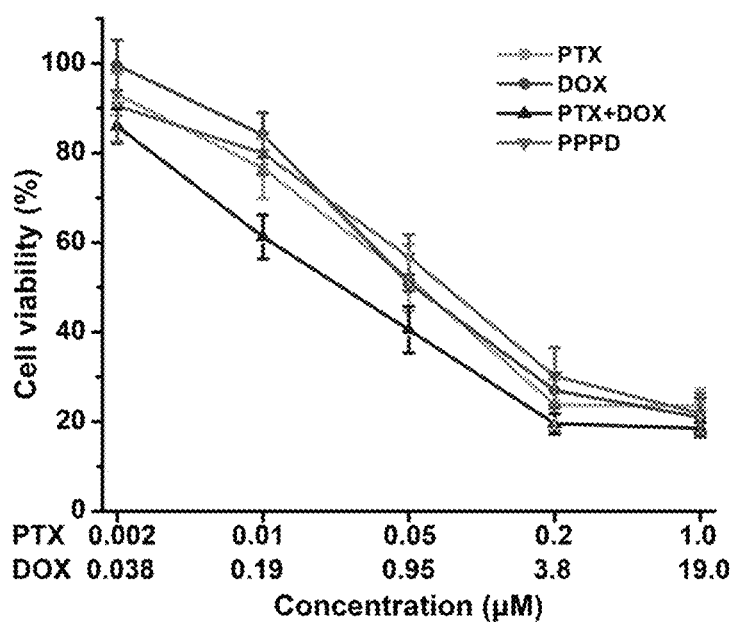
FIG. 13 illustrates cell viability of SKOV-3 cells after various treatments with free PTX, free DOX, a combination of PTX and DOX, and PPPD nanogels for 72 hours.
Figure 14:
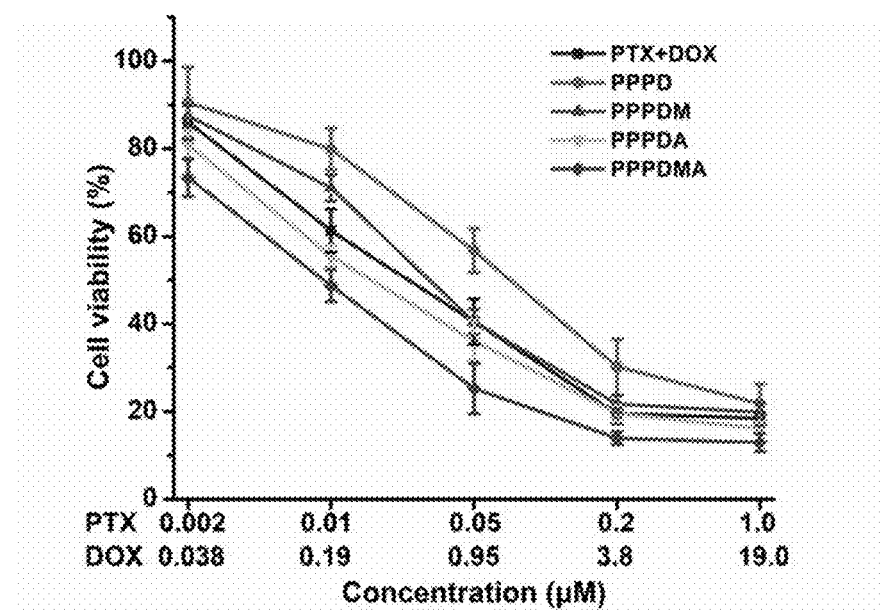
FIG. 14 illustrates cell viability of SKOV-3 cells after various treatments with the combination of free PTX and DOX, PPPD, PPPDM, PPPDSA, and PPPDMA nanogels for 72 hours.

To investigate whether the enhanced cellular uptake of PPPDMA could yield a better cell-killing effect, a cell proliferation assay was employed. FIG. 13 confirmed that the combination of free PTX and DOX is more potent than either PTX or DOX alone in killing SKOV-3 cells. Since the non-targeted PPPD nanogel is less efficient in entering cancer cells (FIG. 12), the cell-killing efficacy is lower than that of free drug combination (FIG. 13). With the help of targeting ligands, both mono-targeted nanogels, PPPDM and PPPDA, exhibited a better cell-killing effect than non-targeted PPPD (FIG. 14). As expected, the PPPDMA displayed the highest potency in killing cancer cells ($IC_{50}$ of 6.5 nM for PTX and 123.5 nM for DOX, respectively).

Figure 15:
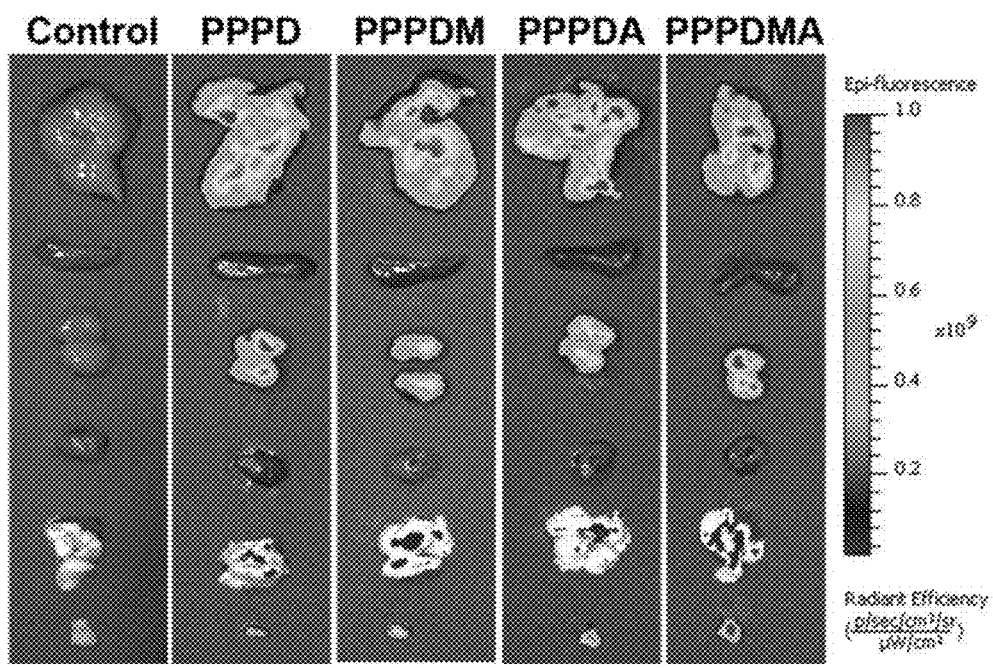
FIG. 15 illustrates biodistribution of the nanogels in a peritoneal metastatic ovarian tumor mouse model. Ex vivo images of mice organs and tumors after treatments with various nanogels.

2.4. Analysis of Mice Organs and Tumors In Vivo after Various Nanogel Treatments A mouse peritoneal metastatic ovarian tumor model was established by inoculating luciferase-expressing SKOV-3 (SKOV-3/Luc) cells intraperitoneally into female nude mice. Since the bioluminescence intensity is proportional to the population of SKOV-3/Luc cells in tumor, the size and distribution of tumors could be monitored by recording the intensity of bioluminescence emitted from mice after the injection of luciferin. Besides serving as an active pharmaceutical ingredient, DOX in the nanogel can also be used as a fluorescent probe. Thus, the biodistribution of nanogel can be tracked with the help of a non-invasive In Vivo Imaging System (IVIS). It was found that the fluorescent emission of DOX was observed mainly in the livers, kidneys, and tumors of nanogel treated mice (FIG. 15). As expected, nanogels with MBA or AEB ligands were more effective in targeting tumor tissue as evidenced by stronger fluorescent signals. The strongest fluorescent signal was detected in the tumor of the PPPDMA treated mice.

Figure 16:
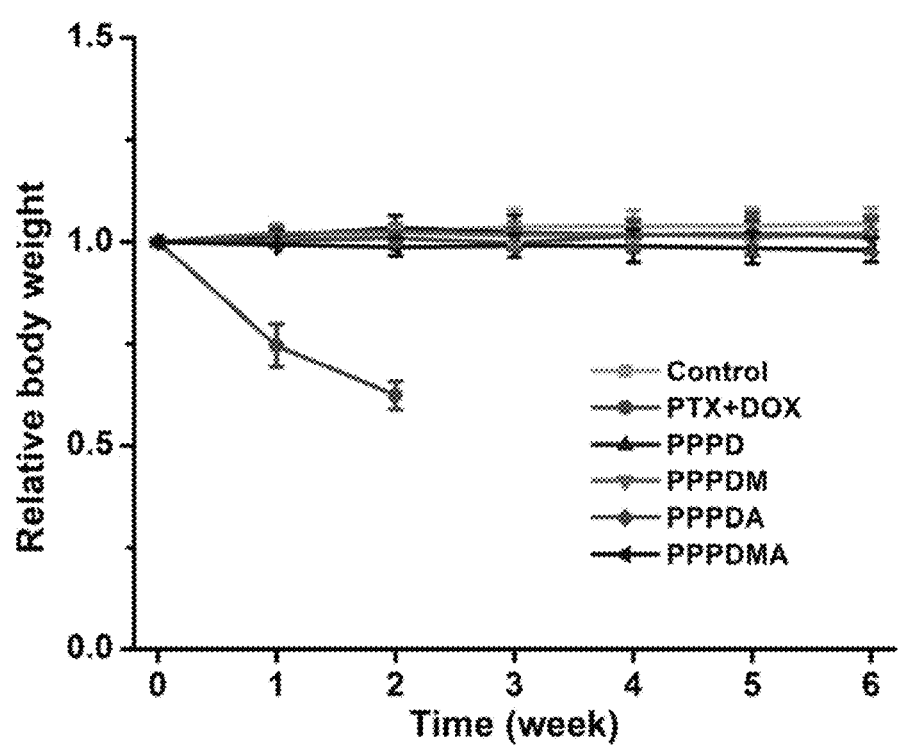
FIG. 16 illustrates body weight changes in the duration of the treatments with various nanogels.

In the in vivo anticancer efficacy assay, tumor-bearing nude mice were intraperitoneally administrated with one of the following groups: control (PBS), PTX+DOX (the free drug combination of DOX and PTX in the formulation of TAXOL® (paclitaxel)), PPPD, PPPDM, PPPDA, and PPPDMA nanogels, at a combination dose of 1.0 mg/kg equivalent to PTX and 12 mg/kg equivalent to DOX, corresponding to a 1:19 molar ratio between PTX and DOX. Such a combination dose is higher than the reported combination maximum tolerated dose (MTD) of the two drugs (1.0 mg/kg PTX plus 1.5 mg/kg DOX) for nude mice. It has been reported that a lower combination dosage of 5.0 mg/kg (PTX+DOX in total) could cause over 30% body weight loss to mice in 10 days because of the elevated toxic side effects of the drug cocktail. As a result, mice in the free PTX+DOX treatment group exhibited drastic body weight loss (about 25%) in a week, as shown in FIG. 16, and died within two weeks. On the contrary, no obvious body weight loss was observed in mice of the other groups even after six weeks of treatment.

Figure 17:
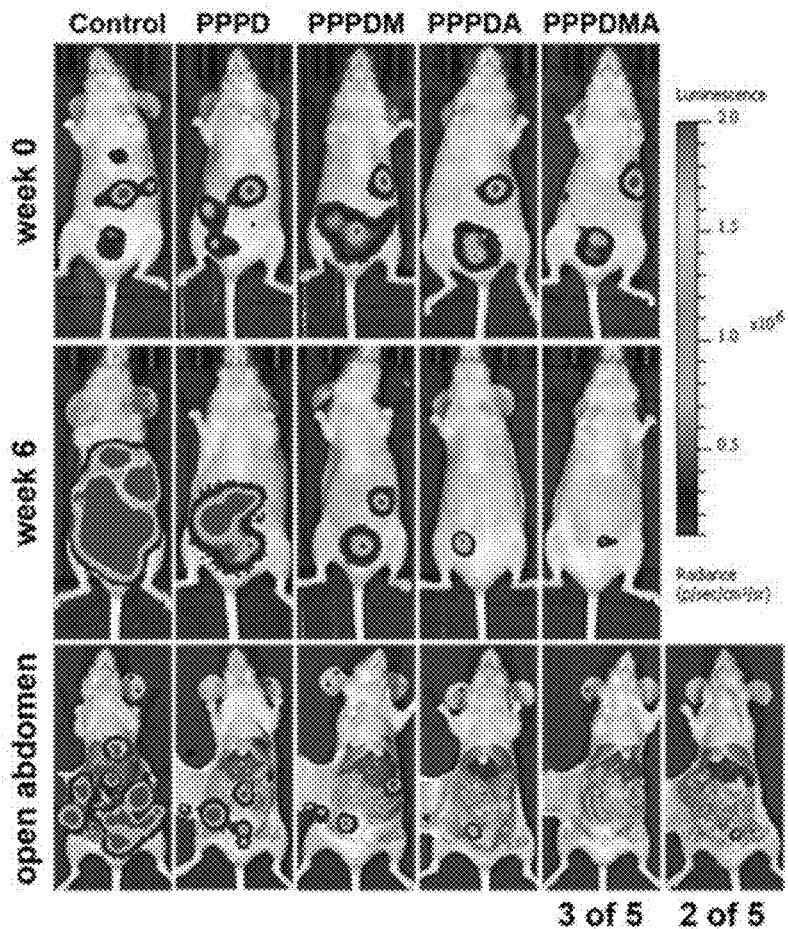
FIG. 17 shows representative whole-body bioluminescence images of mice before and after various treatments for 6 weeks.
Figure 18:
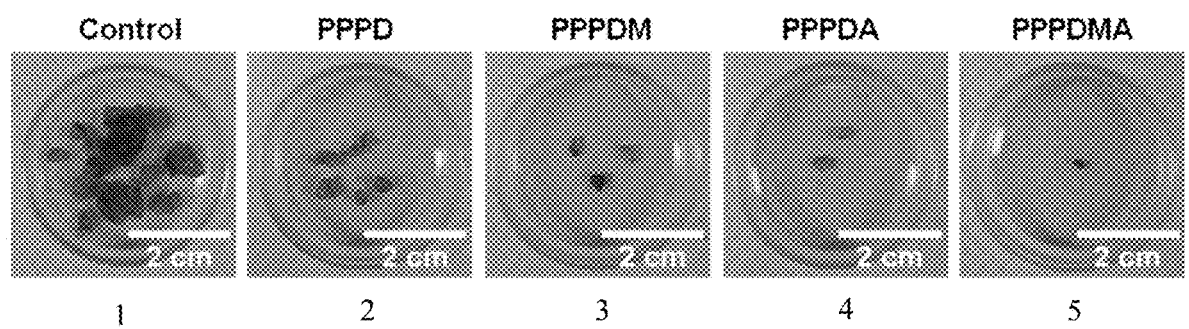
FIG. 18 shows representative images of tumors harvested from sacrificed mice after receiving different treatments for 6 weeks.
Figure 19:
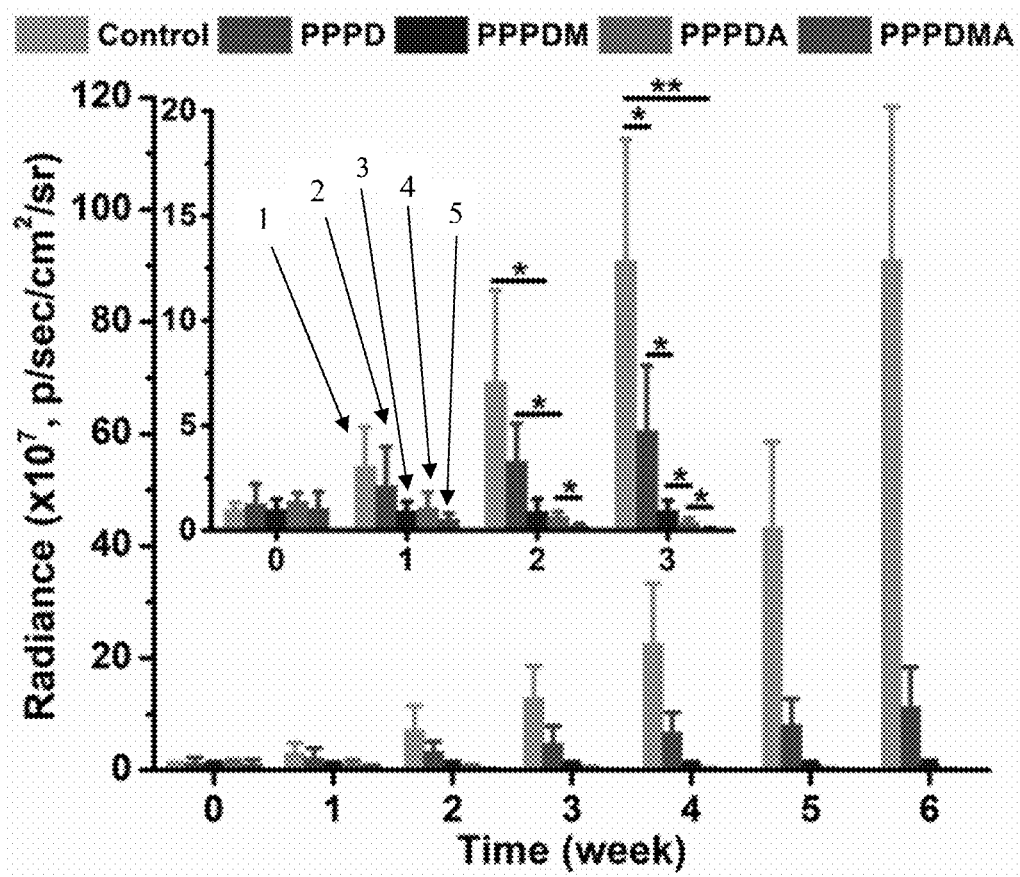
FIG. 19 illustrates bioluminescent intensity of mice at predetermined weekly time points, where the inset: enlargement corresponding to the first 3 weeks, and where data represent the means±SD, n=5, for *P<0.05; P<0.01; and *P<0.001.
Figure 20:
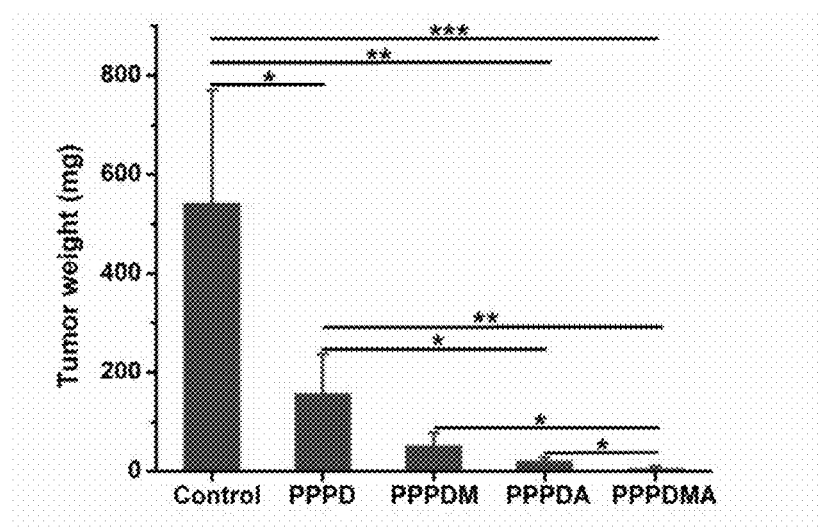
FIG. 20 show tumor weight of mice after receiving different treatments for 6 weeks, where data represent the means±SD, n=5, for *P<0.05; P<0.01; and *P<0.001.
Figure 21:
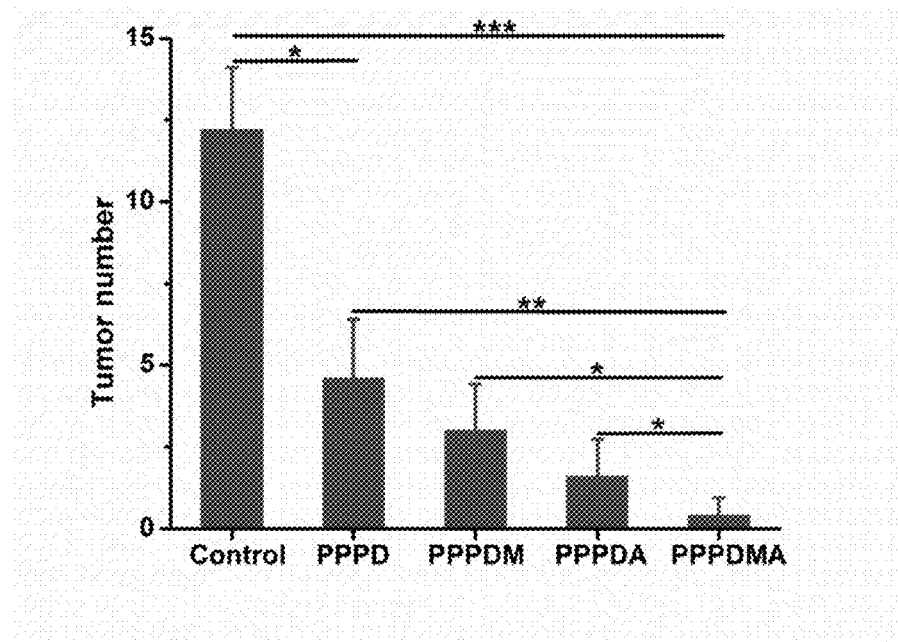
FIG. 21 show tumor number in mice after receiving different treatments for 6 weeks, where data represent the means±SD, n=5, for *P<0.05; P<0.01; and *P<0.001.

Aside from reducing the toxic side effects of the combined drugs, the drug-loaded nanogels also presented plausible tumor growth inhibition to varying degrees. As shown in FIG. 17, for mice treated with PBS in the control group, strong luminescent signals covered nearly the entire abdominal area of the mice after 6 weeks of treatment, indicating tumors had spread all over the abdomen of the mice. The rapid tumor growth was also quantitatively reflected by the dramatic increase in the luminescent intensity of mice, as shown in FIG. 19. However, in contrast to the control group, the non-targeted PPPD nanogels treatment considerably delayed the tumor growth, as seen by the luminescent signals only being detected in about a quarter of the abdomen area of mice (FIG. 17), and the luminescent intensity was much weaker (FIG. 19). The almost constant luminescent intensity throughout the PPPDM treatment group proved its efficacy in controlling the growth of the tumor (FIGS. 17 and 19). Furthermore, it was revealed that PPPDA was even more efficient in inhibiting tumor growth, as evidenced by the progressively reduced luminescent signals (FIGS. 17 and 19). Most importantly, among all groups, the PPPDMA exhibited the highest potency in inhibiting the progression of tumors. In this group, after 6 weeks of treatment, the mice emitted little-to-no luminescent signals. As presented in FIGS. 17, 18, and 20, a very faint bioluminescent signal was observed in 2 of the 5 PPPDMA treated mice, while no detectable bioluminescent signal was recorded in the other 3 mice, indicating the eradication of the disease. To quantify the efficacies of different treatments in more detail, tumors were harvested for analysis after the mice were sacrificed. As shown in FIG. 18, more than 10 solid tumors were collected from the abdominal cavity of mice in the control group. In contrast, significantly fewer tumors were found in mice treated with the PPPD nano-cocktail, and the tumor sizes were smaller than those in control group, which were also quantitatively evidenced by the dramastically reduced tumor weight (FIG. 20) and tumor numbers (FIG. 21).

Figure 22:
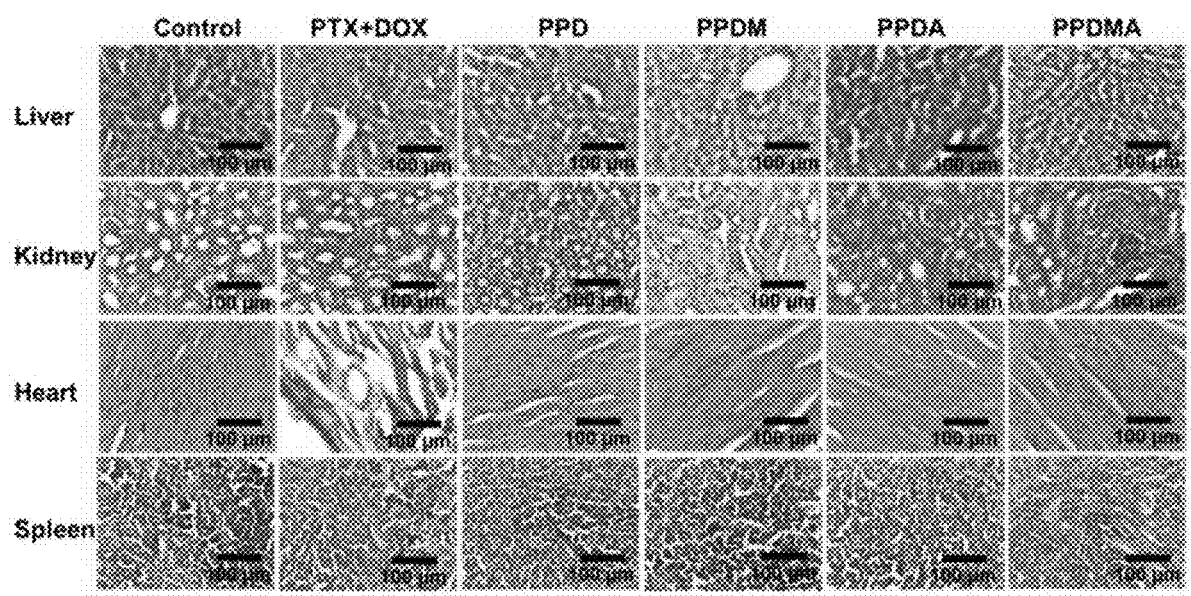
FIG. 22 shows H&E-stained images of livers, kidney, heart, and spleens from different treatment groups.

To evaluate the potential systemic toxicity of the nano-cocktail, histological analysis of the liver, kidney, heart, and spleen were carried out. Compared with the control group, no obvious structure difference was detected in the livers, kidneys, and spleens from other treatment groups (FIG. 22). However, the heart tissue from the animals treated with free drug combination contains lots of empty space and disoriented structure, indicating the severe cardiotoxicity of the treatment.

3. Discussion

Cancer cell migration and metastasis significantly reduce the survival rate of ovarian cancer patients. Ovarian cancer is nearly undetectable until it metastasizes in the later stages, requiring comprehensive treatment to fully eradicate. Research has shown a need for an effective, targeted drug to eradicate this cancer, hence, SKOV-3 ovarian cancer cells were used for the model of this study.

Herein, we designed an ErbB2 receptor and sigma 2 receptor hetero-targeted dual-responsive nano-cocktail (PPPDMA) to deliver both paclitaxel (PTX) and doxorubicin (DOX) into a tumor tissue with a cancer cell responsive, traceless linking strategy. Once PPPDMA enters cancer cells through the multivalent effect of its hetero-ligands, the conjugated PTX and DOX will be tracelessly released upon the intracellular high redox and ROS levels, and subsequently eradicate the cancer cells. High-performance liquid chromatography (HPLC) confirmed that both free PTX and the released compound from the nanogel under reducing or elevated ROS level environment have the same elution time. Furthermore, the signal peak of PTX was also confirmed by liquid chromatography-mass spectrometry (LC-MS) in the released product. Similar results also were observed for the released DOX under reducing or elevated ROS level environment.

Figure 8:
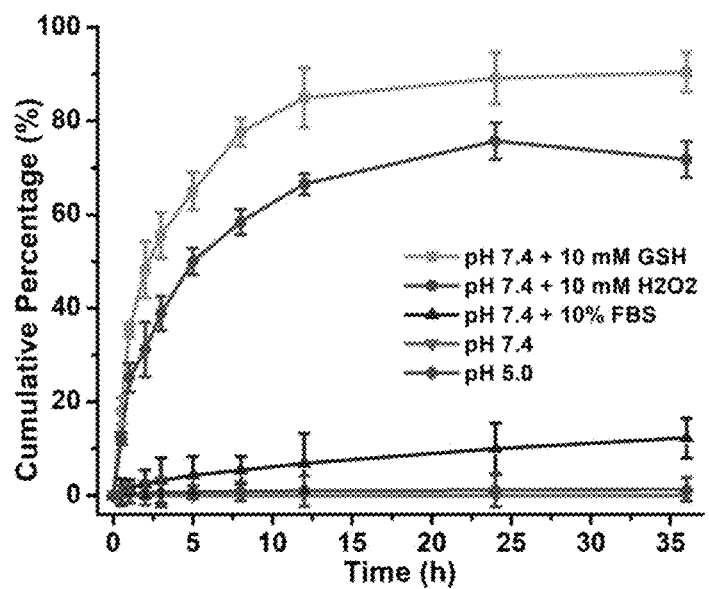
FIG. 8 shows drug release profiles of DOX from PPD nanogels.

FIGS. 8 and 9 show the stability of the nanogel during normal blood circulation. The outstanding stability of the nanogel ensures it will not release its payloads prematurely during blood circulation, while its responsiveness to GSH and elevated ROS bestows the capability of tracelessly dumping more PTX and DOX inside cancer cells than the processing capacity of P-gp efflux pump of the cells and ultimately kill them.

To facilitate the nanogels entering ovarian cancer cells, 4-Methoxybenzamide (MBA) which targets sigma 2 receptors and Anti-ErbB2 AFFIBODY® (AEB) molecule which targets ErbB2 receptors were conjugated onto the surface of the nanogel separately. While it was shown that the increase in ligand density could boost the killing effect, there was a ligand density limit wherein additional potency could not be achieved. The inventors reached the conclusion that when the ligand density of the nanogels is greater than or equal to the density of its corresponding receptor, the cellular uptake of the nanogel is limited by the receptors expressed on the cell surface. Thus, further addition of targeting ligands cannot yield enhanced efficacy. To break the receptor density limitation of mono-ligands, a hetero-dual targeting strategy was adopted by conjugating both MBA and AEB onto the surface of the PPPD nanogel simultaneously. Based on the results, it can be concluded that the hetero-ligand strategy facilitates PPPDMA entering cancer cells and boosts its potency in killing cancer cells.

Based upon the above in vitro results, the inventors further investigated the tumor targeting and growth inhibitory effect of PPPDMA in vivo. The mouse peritoneal metastatic ovarian tumor model was established using the SKOV-3 ovarian cancer cells places within female nude mice. The appearance of a fluorescent emission of DOX observed in the livers, kidneys and tumors in FIG. 15 suggests that the nanogels could take advantage of the Enhanced Permeability and Retention effect, wherein molecules of a certain size (such as liposomes, nanoparticles, and macromolecular drugs) tend to accumulate in tumor tissue more than normal tissue. Such a response is supplemented by the stronger fluorescent signals from MBA and AEB infused nanogels, with the strongest signal given by PPPDMA, indicating the success of a hetero-targeted nano-cocktail. Furthermore, FIG. 16 indicated a strong indication of reduced systemic toxicity. While mice in the free PTX+DOX group died within 2 weeks, the lack of observed body weight loss in mice of the other groups indicates that the formulation of nanogels could effectively circumvent the severe systemic toxicity of the free drug combination. Such results can be attributed to the targeted drug delivery of the drug cocktail, thereby attacking only cancerous cells within a region.

As expected, all targeted nano-cocktail treatments further diminished the tumor burden both in tumor number and in tumor size. Specifically, compared with the control group, the hetero-targeted PPPDMA treatment reduced its tumor burden over 99% (in tumor weight) and 96% (in tumor number). Most importantly, only one tiny solid tumor was collected in 2 mice in the PPPDMA treatment group, while no detectable tumor was present in the other 3. These results are in agreement with those obtained from bioluminescence analysis (FIG. 17), which collectively display the efficacy of the dual-drug, dual-responsiveness, and hetero-targeting strategy in treating ovarian cancer. Furthermore, histological analysis showed none of the nano-cocktail treatments resulted in disrupted cardiac structure, which confirmed that targeted, traceless release technology effectively attenuated the DOX-associated cardiotoxicity.

4. Conclusion

In summary, the invention pertains to a hetero-targeted, dual-responsive nano-cocktail system (i.e., the PPPDMA nanogel) which is safe and effective when eradiating cancer in a metastatic ovarian tumor model. Due to the existence of covalent linkages between the polymer and the drugs, the PPPDMA nanogel is premature-release-free during circulation in the blood stream. With the help of MBA and anti-ErbB2 AFFIBODY® molecule, PPPDMA can selectively enter tumor tissue and cancer cells. Upon the trigger of elevated redox potential and ROS in the cytoplasm of cancer cells, PPPDMA can tracelessly release its payloads, PTX and DOX. Consequently, the integration of the hetero-targeting, cancer cell environment responsive release, traceless linking, and drug cocktail concepts synergistically enhances the anticancer efficacy of PPPDMA while eliminating the systemic toxicity of the drug cocktail. More importantly, due to the interchangeable nature of the payload and targeting ligands, the results pave the way for developing a safe and effective delivery platform for the eradicating of other cancers.

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged both in whole or in part. Furthermore, those of ordinary skill in the art will appreciate that the foregoing description is by way of example only and is not intended to limit the invention so further described in the appended claims.

What is claimed is:

1. A nanogel for use as a drug cocktail, wherein the nanogel comprises a first chemotherapeutic agent, a second chemotherapeutic agent, a first targeting ligand, and a second targeting ligand, wherein the nanogel further comprises a traceless linker comprising a disulfide bond; wherein the nanogel comprises a polymeric carrier comprising a copolymer of an ethyl acrylate and an ethylene oxide, wherein the ethyl acrylate comprises poly[(2-(pyridin-2-yldisulfanyl) ethyl acrylate), (pyridine-2-thiol)ethyl acrylate, (pyridine-2-thiol) ethyl methacrylate, ethyl (2-(pyridin-2-yldisulfanyl) ethyl) carbonate, N-(2-(pyridin-2-yldisulfanyl)ethyl) acrylamide, or a combination thereof; wherein the first and second targeting ligands are selected from the group consisting of 4-methoxybenzamide, Anti-ErbB2 antibody, Anti-EGFR antibody, folic acid, β-d-glucose, Asn-Gly-Arg peptide, Angiopep2, Herceptin, transferrin, Arg-Gly-Asp peptide, lactobionic acid, or a combination thereof; and wherein the first and second chemotherapeutic agents are covalently linked to the polymeric carrier via the traceless linker.

2. The nanogel of claim 1, wherein the ethylene oxide comprises polyethylene glycol.

3. The nanogel of claim 1, wherein the first chemotherapeutic agent is different from the second chemotherapeutic agent.

4. The nanogel of claim 3, wherein the first chemotherapeutic agent and the second chemotherapeutic agent are selected from the group consisting of doxorubicin, paclitaxel, daunorubicin, valrubicin, triptolide, epirubicin, idarubicin, docetaxel, cisplatin, carboplatin, oxaliplatin, camptothecin, vincristine, vinblastine, 5-fluorouracil (5-FU), mitomycin, cyclophosphamide, methotrexate, mitoxantrone, topotecan, capecitabine, doxifluridine, irinotecan, tegafur, chlorambucil, belotecan, anastrozole, tamoxifen, imatinib, floxuridine, leuprolide, flutamide, zoledronate, streptozocin, vinorelbine, hydroxyurea, retinoic acid, mechlorethamine, busulfan, prednisone, testosterone, aspirin, salicylates, ibuprofen, naproxen, fenoprofen, indomethacin, phenyltazone, mechlorethamine, dexamethasone, prednisolone, celecoxib, valdecoxib, nimesulide, cortisone, corticosteroid, gemcitabine, cedrol, or a combination thereof.

5. The nanogel of claim 1, wherein the first chemotherapeutic agent comprises a taxane.

6. The nanogel of claim 5, wherein the taxane comprises paclitaxel.

7. The nanogel of claim 1, wherein the second chemotherapeutic agent comprises an anthracycline.

8. The nanogel of claim 7, wherein the anthracycline comprises doxorubicin.

9. The nanogel of claim 1, wherein the first targeting ligand is different from the second targeting ligand.

10. The nanogel of claim 1, wherein the first targeting ligand comprises 4-methoxybenzamide and the second targeting ligand comprises Anti-ErbB2 antibody.

11. The nanogel of claim 1, wherein the molar ratio of the first chemotherapeutic agent to the second chemotherapeutic agent ranges from about 1:1 to about 1:1000.

12. The nanogel of claim 1, wherein the average particle size of the nanogel ranges from about 50 nanometers to about 150 nanometers.

13. The nanogel of claim 1, wherein the nanogel has a surface charge ranging from about −1 millivolts to about −50 millivolts.

14. A method of treating a cancerous area in a mammal utilizing targeting ligands to target only cancerous cells within the cancerous area, the method comprising:
delivering a nanogel having traceless linkers to the cancerous area, wherein more than one chemotherapeutic agent is then released from the nanogel, the nanogel comprising a polymeric carrier; a first chemotherapeutic agent, a second chemotherapeutic agent that is different from the first chemotherapeutic agent, a first targeting ligand, and a second targeting ligand that is different from the first targeting ligand, wherein the nanogel further comprises a traceless linker comprising a disulfide bond; wherein the nanogel comprises a polymeric carrier comprising a copolymer of an ethyl acrylate and an ethylene oxide, wherein the ethyl acrylate comprises poly[(2-(pyridin-2-yldisulfanyl) ethyl acrylate), (pyridine-2-thiol)ethyl acrylate, (pyridine-2-thiol) ethyl methacrylate, ethyl (2-(pyridin-2-yldisulfanyl)ethyl) carbonate, N-(2-(pyridin-2-yldisulfanyl)ethyl) acrylamide, or a combination thereof; wherein the first and second targeting ligands are selected from the group consisting of 4-methoxybenzamide, Anti-ErbB2 antibody, Anti-EGFR antibody, folic acid, β-d-glucose, Asn-Gly-Arg peptide, Angiopep2, Herceptin, transferrin, Arg-Gly-Asp peptide, lactobionic acid, or a combination thereof; and wherein the first and second chemotherapeutic agents are covalently linked to the polymeric carrier via the traceless linker,
wherein the nanogel further comprises a traceless linker comprising a disulfide bond.

15. The method of claim 14, wherein the first targeting ligand is a benzamide comprising 4-methoxybenzamide.

16. The method of claim 14, wherein the second a targeting ligand comprises Anti-ErbB2 antibody.

17. The method of claim 14, wherein the first chemotherapeutic agent and the second chemotherapeutic agent are selected from the group consisting of doxorubicin, paclitaxel, daunorubicin, valrubicin, triptolide, epirubicin, idarubicin, docetaxel, cisplatin, carboplatin, oxaliplatin, camptothecin, vincristine, vinblastine, 5-fluorouracil(5-FU), mitomycin, cyclophosphamide, methotrexate, mitoxantrone, topotecan, capecitabine, doxifluridine, irinotecan, tegafur, chlorambucil, belotecan, anastrozole, tamoxifen, imatinib, floxuridine, leuprolide, flutamide, zoledronate, streptozocin, vinorelbine, hydroxyurea, retinoic acid, mechlorethamine, busulfan, prednisone, testosterone, aspirin, salicylates, ibuprofen, naproxen, fenoprofen, indomethacin, phenyltazone, mechlorethamine, dexamethasone, prednisolone, celecoxib, valdecoxib, nimesulide, cortisone, corticosteroid, gemcitabine, cedrol, or a combination thereof.

* * * * *